(12) United States Patent
Leimbach

(10) Patent No.: US 9,463,043 B2
(45) Date of Patent: *Oct. 11, 2016

(54) BIOPSY TARGETING CUBE WITH LIVING HINGES

(71) Applicant: Devicor Medical Products, Inc., Cincinnati, OH (US)

(72) Inventor: Jessica P. Leimbach, Cincinnati, OH (US)

(73) Assignee: Devicor Medical Products, Inc., Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 14/472,473

(22) Filed: Aug. 29, 2014

(65) Prior Publication Data

US 2014/0371627 A1    Dec. 18, 2014

Related U.S. Application Data

(63) Continuation of application No. 12/485,318, filed on Jun. 16, 2009, now Pat. No. 8,858,537.

(51) Int. Cl.
*A61B 10/02* (2006.01)
*A61B 17/34* (2006.01)
(Continued)

(52) U.S. Cl.
CPC ........... *A61B 17/3403* (2013.01); *A61B 5/061* (2013.01); *A61B 10/0266* (2013.01);
(Continued)

(58) Field of Classification Search
CPC ................. A61B 2017/3411; A61B 17/3403; A61B 2017/00762; B29C 45/1676
USPC ....... 600/104, 407, 411, 423, 562, 564, 567; 604/19, 48, 93.01, 116; 606/1, 130, 606/131
See application file for complete search history.

(56) References Cited

U.S. PATENT DOCUMENTS 3,805,770 A    4/1974   Okada
5,056,523 A   10/1991   Hotchkiss, Jr. et al.
(Continued)

FOREIGN PATENT DOCUMENTS

AU    2010202362 A1    1/2011
AU    2010202363 A1    1/2011
(Continued)

OTHER PUBLICATIONS

Australian Office Action dated Nov. 18, 2014 for Application No. AU 2010202362, 3 pgs.
(Continued)

*Primary Examiner* — Aaron Roane
(74) *Attorney, Agent, or Firm* — Frost Brown Todd LLC

(57) ABSTRACT

A biopsy system comprises a control module, a localization assembly, a biopsy device, and a targeting cube. The biopsy device comprises a holster portion and a probe. The probe and/or other associated components are configured to selectively couple with a targeting cube, where the targeting cube is configured to selectively couple with a grid plate having apertures for receiving the targeting cube. The targeting cube comprises a body defined by faces. The targeting cube further comprises guide holes that originate and terminate at the faces and pass through the body of the targeting cube to provide passageways through the targeting cube. The targeting cube further comprises at least one hinged member positioned along the outer portion of the targeting cube and interfacing with an aperture in the grid plate. The hinged member may provide a tapered profile to the targeting cube and may further comprise an elastomeric portion.

8 Claims, 22 Drawing Sheets

(51) Int. Cl.
*A61B 5/06* (2006.01)
*A61B 17/00* (2006.01)
*A61B 19/00* (2006.01)

(52) U.S. Cl.
CPC .... *A61B10/0275* (2013.01); *A61B 2010/0208* (2013.01); *A61B 2017/00796* (2013.01); *A61B 2017/00862* (2013.01); *A61B 2017/3407* (2013.01); *A61B 2017/3411* (2013.01); *A61B 2019/205* (2013.01); *A61B 2019/5236* (2013.01)

(56) References Cited

U.S. PATENT DOCUMENTS

| | | | |
|---|---|---|---|
| 5,105,807 A | 4/1992 | Kahn et al. | |
| 5,217,441 A | 6/1993 | Shichman | |
| 5,526,822 A | 6/1996 | Burbank et al. | |
| 5,534,778 A | 7/1996 | Loos et al. | |
| 5,637,074 A | 6/1997 | Andino et al. | |
| 5,649,547 A | 7/1997 | Ritchart et al. | |
| 5,713,869 A | 2/1998 | Morejon | |
| 5,752,768 A | 5/1998 | Assh | |
| 5,769,086 A | 6/1998 | Ritchart et al. | |
| 5,775,333 A | 7/1998 | Burbank et al. | |
| 5,855,554 A | 1/1999 | Schneider et al. | |
| 5,928,164 A | 7/1999 | Burbank et al. | |
| 5,964,716 A | 10/1999 | Gregoire et al. | |
| 5,980,469 A | 11/1999 | Burbank et al. | |
| 6,007,497 A | 12/1999 | Huitema | |
| 6,017,316 A | 1/2000 | Ritchart et al. | |
| 6,077,230 A | 6/2000 | Gregoire et al. | |
| 6,086,544 A | 7/2000 | Hibner et al. | |
| 6,120,462 A | 9/2000 | Hibner et al. | |
| 6,228,055 B1 | 5/2001 | Foerster et al. | |
| 6,231,522 B1 | 5/2001 | Voegele et al. | |
| 6,270,476 B1 | 8/2001 | Santoianni et al. | |
| 6,273,862 B1 | 8/2001 | Privitera et al. | |
| 6,626,849 B2 | 9/2003 | Huitema et al. | |
| 6,743,177 B2 | 6/2004 | Ito | |
| 6,752,768 B2 | 6/2004 | Burdorff et al. | |
| 7,244,234 B2 | 7/2007 | Ridley et al. | |
| 7,367,973 B2 * | 5/2008 | Manzo | A61B 18/14 604/22 |
| 7,379,769 B2 | 5/2008 | Piron et al. | |
| 7,442,171 B2 | 10/2008 | Stephens et al. | |
| 7,507,210 B2 | 3/2009 | Hibner et al. | |
| 7,740,593 B2 | 6/2010 | Shabaz | |
| 7,831,290 B2 | 11/2010 | Hughes et al. | |
| 7,837,630 B2 | 11/2010 | Nicoson et al. | |
| 7,846,109 B2 | 12/2010 | Parihar et al. | |
| 7,938,786 B2 | 5/2011 | Ritchie et al. | |
| 8,167,814 B2 | 5/2012 | Leimbach et al. | |
| 8,197,495 B2 | 6/2012 | Leimbach et al. | |
| 8,241,302 B2 | 8/2012 | Leimbach et al. | |
| 8,328,732 B2 | 12/2012 | Parihar et al. | |
| 8,366,634 B2 | 2/2013 | Leimbach et al. | |
| 8,480,595 B2 | 7/2013 | Speeg et al. | |
| 8,568,333 B2 | 10/2013 | Hibner et al. | |
| 8,622,927 B2 | 1/2014 | Parihar et al. | |
| 8,702,623 B2 | 4/2014 | Parihar et al. | |
| 8,858,537 B2 | 10/2014 | Leimbach | |
| 2003/0199753 A1 | 10/2003 | Hibner et al. | |
| 2004/0064149 A1 | 4/2004 | Doern et al. | |
| 2005/0096695 A1 | 5/2005 | Olich | |
| 2007/0135821 A1* | 6/2007 | Shabaz | A61B 17/3403 606/130 |
| 2007/0167736 A1 | 7/2007 | Dietz et al. | |
| 2007/0233157 A1 | 10/2007 | Mark et al. | |
| 2008/0214955 A1 | 9/2008 | Speeg et al. | |
| 2009/0131751 A1* | 5/2009 | Spivey | A61B 1/00154 600/114 |
| 2010/0160819 A1 | 6/2010 | Parihar et al. | |

FOREIGN PATENT DOCUMENTS

| | | |
|---|---|---|
| AU | 2010202364 A1 | 1/2011 |
| CN | 101011269 A | 8/2007 |
| CN | 101066215 A | 11/2007 |
| CN | 101325918 A | 12/2008 |
| CN | 101919717 A | 12/2010 |
| CN | 101919718 A | 12/2010 |
| CN | 101919719 A | 12/2010 |
| CN | 101919734 A | 12/2010 |
| CN | 101919735 A | 12/2010 |
| CN | 103932762 A | 7/2014 |
| EP | 0 640 842 A1 | 3/1995 |
| EP | 1 027 867 A1 | 8/2000 |
| EP | 1 759 645 A1 | 3/2007 |
| EP | 1 815 815 A1 | 8/2007 |
| EP | 1 852 076 A1 | 11/2007 |
| EP | 2 263 579 A1 | 12/2010 |
| EP | 2 266 477 A2 | 12/2010 |
| EP | 2 266 478 A2 | 12/2010 |
| EP | 2 266 479 A2 | 12/2010 |
| EP | 2 266 480 A2 | 12/2010 |
| EP | 2 324 782 A1 | 5/2011 |
| EP | 2 324 783 A1 | 5/2011 |
| JP | 2007-296343 A | 11/2007 |
| JP | 2007-296344 A | 11/2007 |
| JP | 5676150 B2 | 2/2015 |
| JP | 5680345 B2 | 3/2015 |
| JP | 5762695 B2 | 8/2015 |
| KR | 10-2008-0082669 A | 9/2008 |
| WO | WO 02/13709 A1 | 2/2002 |
| WO | WO 03/039386 A1 | 5/2003 |
| WO | WO 2007/070285 A2 | 6/2007 |
| WO | WO 2009/047494 A1 | 4/2009 |

OTHER PUBLICATIONS

Australian Office Action dated Nov. 18, 2014 for Application No. AU 2010202363, 3 pgs.
Australian Office Action dated Nov. 25, 2014 for Application No. AU 2010202364, 3 pgs.
Chinese Office Action dated Sep. 10, 2013 for Application No. CN 201010208874.8, 7 pgs.
Chinese Office Action dated Dec. 6, 2013 for Application No. CN 201010208874.8, 5 pgs.
Chinese Office Action dated Nov. 27, 2013 for Application No. CN 201010205294.3, 9 pgs.
Chinese Office Action dated Jul. 3, 2014 for Application No. CN 201010205294.3, 9 pgs.
Chinese Office Action dated Nov. 11, 2013 for Application No. CN 101010205292.4, 7 pgs.
Chinese Office Action dated Sep. 16, 2013 for Application No. CN 201010205282.0, 7 pgs.
Chinese Office Action dated Dec. 17, 2013 for Application No. CN 201010208886.0, 7 pgs.
Chinese Office Action dated May 16, 2014 for Application No. CN 201010208886.0, 3 pgs.
Chinese Office Action dated Jul. 24, 2015 for Application No. CN 201410154203.6, 6 pgs.
European Search Report and Written Opinion dated Aug. 8, 2007 for Application No. 07251810.3, 6 pgs.
European Search Report and Written Opinion dated Aug. 28, 2007 for Application No. 07251817.8, 9 pgs.
European Search Report and Written Opinion dated Feb. 28, 2012 for Application No. EP 10251099.7, 7 pgs.
European Search Report and Written Opinion dated Feb. 28, 2012 for Application No. EP 10251095.5, 8 pgs.
European Search Report and Written Opinion dated Feb. 28, 2012 for Application No. EP 10251102.9, 8 pgs.
European Search Report and Written Opinion dated Feb. 29, 2012 for Application No. EP 10251096.3, 8 pgs.
European Search Report and Written Opinion dated Feb. 29, 2012 for Application No. EP 10251100.3, 8 pgs.
European Communication dated May 4, 2015 for Application No. EP 10251100.3, 5 pgs.

(56) References Cited

OTHER PUBLICATIONS

European Communication dated Feb. 25, 2016 for Application No. EP 10251100.3, 63 pgs.
Japanese Office Action dated Aug. 21, 2014 for Application No. JP 2010-135904, 2 pgs.
Japanese Office Action dated Aug. 22, 2014 for Application No. JP 2010-135869, 3 pgs.
Japanese Office Action dated Aug. 25, 2014 for Application No. JP 2010-135890, 4 pgs.
Korean Office Action dated Jan. 7, 2016 for Application No. KR 10-2010-0056428, 16 pgs.
Korean Office Action dated Jan. 7, 2016 for Application No. KR 10-2010-0056427, 13 pgs.
Korean Office Action dated Jan. 20, 2016 for Application No. KR 10-2010-0056423, 12 pgs.
U.S. Appl. No. 60/874,792, filed Dec. 13, 2006.
U.S. Appl. No. 60/869,736, filed Dec. 13, 2006.
Canadian Office Action dated Jun. 16, 2016 for U.S. Appl. No. 2,707,268, 4 pgs.
Canadian Office Action dated Jun. 27, 2016 for Application No. 2,707,430, 4 pgs.
Canadian Office Action dated Jun. 21, 2016 for Application No. 2,707,570, 4 pgs.
Korean Office Action, Notice of Final Rejection, dated Jul. 19, 2016 for Application No. 10-2010-0056428, 2 pgs.

\* cited by examiner

BIOPSY TARGETING CUBE WITH LIVING HINGES

This application is a continuation of U.S. patent application Ser. No. 12/485,318, published as U.S. Patent Application Pub. No. 2010/0317994, entitled "Biopsy Targeting Cube with Living Hinges," filed Jun. 16, 2009.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. Merely exemplary biopsy devices are disclosed in U.S. Pat. No. 6,273,862, entitled "Surgical Device for the Collection of Soft Tissue," issued Aug. 14, 2001; U.S. Pat. No. 6,231,522, entitled "Biopsy Instrument with Breakable Sample Segments," issued May 15, 2001; U.S. Pat. No. 6,228,055, entitled "Devices for Marking and Defining Particular Locations in Body Tissue," issued May 8, 2001; U.S. Pat. No. 6,120,462, entitled "Control Method for an Automated Surgical Biopsy Device," issued Sep. 19, 2000; U.S. Pat. No. 6,086,544, entitled "Control Apparatus for an Automated Surgical Biopsy Device," issued Jul. 11, 2000; U.S. Pat. No. 6,077,230, entitled "Biopsy Instrument with Removable Extractor," issued Jun. 20, 2000; U.S. Pat. No. 6,017,316, entitled "Vacuum Control System and Method for Automated Biopsy Device," issued Jan. 25, 2000; U.S. Pat. No. 6,007,497, entitled "Surgical Biopsy Device," issued Dec. 28, 1999; U.S. Pat. No. 5,980,469, entitled "Method and Apparatus for Automated Biopsy and Collection of Soft Tissue," issued Nov. 9, 1999; U.S. Pat. No. 5,964,716, entitled "Method of Use for a Multi-Port Biopsy Instrument," issued Oct. 12, 1999; U.S. Pat. No. 5,928,164, entitled "Apparatus for Automated Biopsy and Collection of Soft Tissue," issued Jul. 27, 1999; U.S. Pat. No. 5,775,333, entitled "Apparatus for Automated Biopsy and Collection of Soft Tissue," issued Jul. 7, 1998; U.S. Pat. No. 5,769,086, entitled "Control System and Method for Automated Biopsy Device," issued Jun. 23, 1998; U.S. Pat. No. 5,649,547, entitled "Methods and Devices for Automated Biopsy and Collection of Soft Tissue," issued Jul. 22, 1997; U.S. Pat. No. 5,526,822, entitled "Method and Apparatus for Automated Biopsy and Collection of Soft Tissue," issued Jun. 18, 1996; U.S. Pub. No. 2008/0214955, entitled "Presentation of Biopsy Sample by Biopsy Device," published Sep. 4, 2008; U.S. Pub. No. 2007/0255168, entitled "Grid and Rotatable Cube Guide Localization Fixture for Biopsy Device," published Nov. 1, 2007; U.S. Pub. No. 2007/0118048, entitled "Remote Thumbwheel for a Surgical Biopsy Device," published May 24, 2007; U.S. Pub. No. 2005/0283069, entitled "MRI Biopsy Device Localization Fixture," published Dec. 22, 2005; U.S. Pub. No. 2003/0199753, entitled "MRI Compatible Biopsy Device with Detachable Probe," published Oct. 23, 2003; U.S. Pub. No. 2003/0109803, entitled "MRI Compatible Surgical Biopsy Device," published Jun. 12, 2003; U.S. Provisional Patent Application Ser. No. 60/874,792, entitled "Biopsy Sample Storage," filed Dec. 13, 2006; and U.S. Provisional Patent Application Ser. No. 60/869,736, entitled "Biopsy System," filed Dec. 13, 2006. The disclosure of each of the above-cited U.S. Patents, U.S. Patent Application Publications, and U.S. Provisional Patent Applications is incorporated by reference herein.

Some biopsy systems may provide an apparatus to guide a probe and/or other components of a biopsy device to a desired biopsy site. In some such biopsy systems, a guide cube and positioning grid plate may be used. The guide cube may be selectively located within an opening in the grid plate. The guide cube may include guide holes to receive a portion of the probe and/or other components, for example a needle, cannula, obturator, or combinations of these or other components. With the guide cube inserted in the grid plate, the probe or other components can be guided through a selected guide hole of the guide cube to arrive at a desired biopsy site. The desired biopsy site may or may not have been identified and/or targeted by one or more of the guidance approaches mentioned above. In some situations, it might be desirable to provide a guide cube with features that improve a guide cube's use with one or more positioning grid plates.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

As shown in the figures, an exemplary magnetic resonance imaging (MRI or MR imaging) compatible biopsy system may include a control module (12), localization assembly (15), and biopsy device (14). In particular, localization assembly (15) is configured to localize a patient's breast and guide needle (90) of biopsy device (14) to a targeted area within the patient's breast; while control module (12) is operable to control biopsy device (14) after needle (90) has been introduced to the target site. These components and their sub-components will be discussed further below. In addition, guide cubes for use with various localization assemblies will be discussed. While this disclosure may reference the biopsy system as compatible with MRI and MRI equipment and devices, it should be appreciated that other imaging techniques and equipment and devices may be used with the components described below, including but not limited to stereotactic, ultrasound, PEM, BSGI, and/or other imaging techniques and equipment.

I. Control Module

Figure 1:
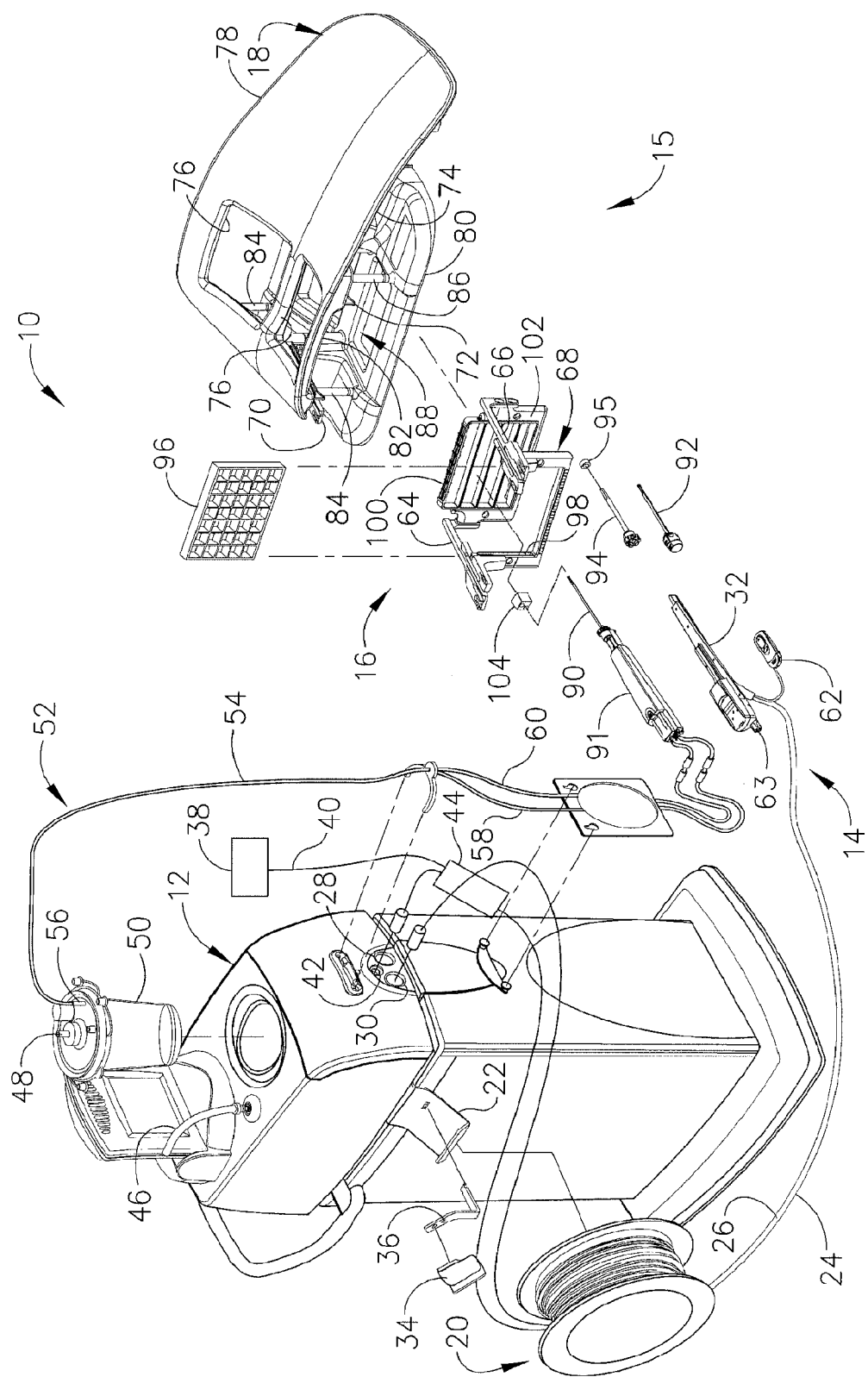
FIG. 1 is a perspective view of a biopsy system including a control module remotely coupled to a biopsy device, and including a localization assembly.
Figure 2:
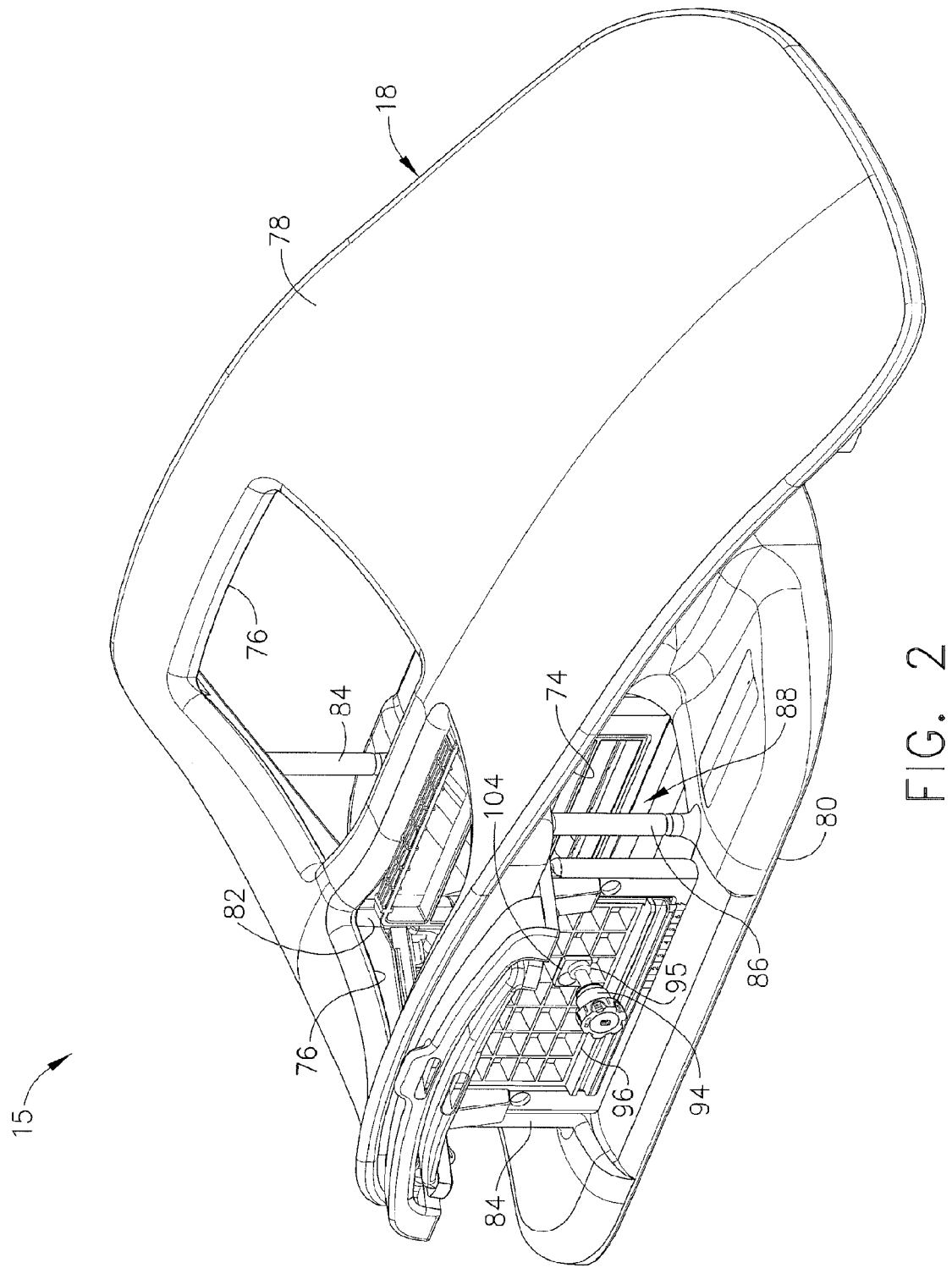
FIG. 2 is a perspective view of a breast coil of the localization assembly of FIG. 1.
Figure 3:
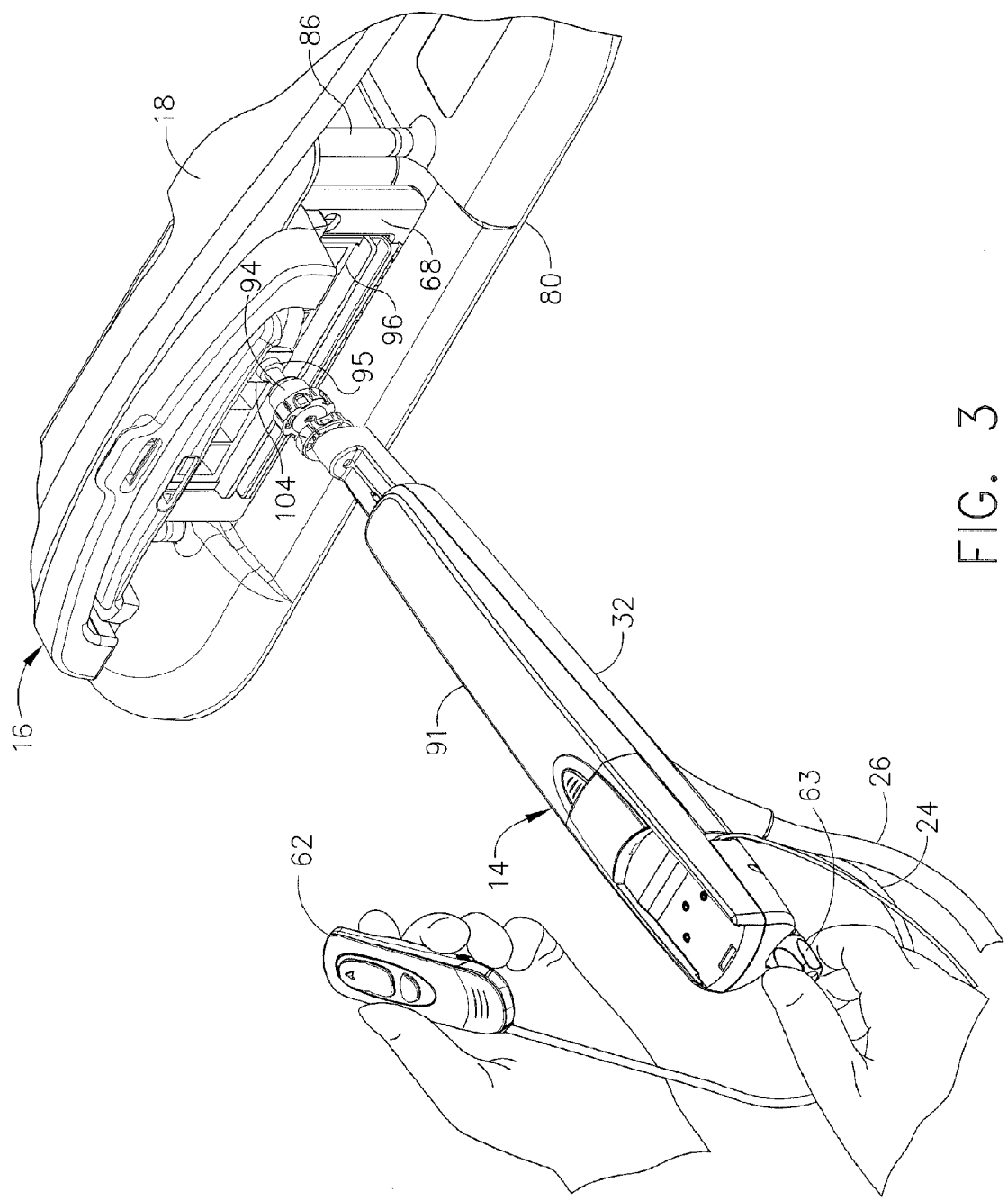
FIG. 3 is a perspective view of the biopsy device inserted through the guide cube of the localization assembly of FIG. 1.

In FIGS. 1-3, MRI compatible biopsy system (10) has control module (12) that may be placed outside of a shielded room containing an MRI machine (not shown) or at least spaced away to mitigate detrimental interaction with its strong magnetic field and/or sensitive radio frequency (RF) signal detection antennas. As described in U.S. Pat. No. 6,752,768, which is hereby incorporated by reference in its entirety, a range of preprogrammed functionality may be incorporated into control module (12) to assist in taking tissue samples. Control module (12) controls and powers biopsy device (14) that is used with localization assembly (15). Biopsy device (14) is positioned and guided by localization fixture (16) attached to breast coil (18) that may be placed upon a gantry (not shown) of a MRI or other imaging machine.

In the present example, control module (12) is mechanically, electrically, and pneumatically coupled to biopsy device (14) so that components may be segregated that need to be spaced away from the strong magnetic field and the sensitive RF receiving components of a MRI machine. Cable management spool (20) is placed upon cable management attachment saddle (22) that projects from a side of control module (12). Wound upon cable management spool (20) is paired electrical cable (24) and mechanical cable (26) for communicating control signals and cutter rotation/advancement motions respectively. In particular, electrical and mechanical cables (24, 26) each have one end connected to respective electrical and mechanical ports (28, 30) in control module (12) and another end connected to holster portion (32) of biopsy device (14). Docking cup (34), which may hold holster portion (32) when not in use, is hooked to control module (12) by docking station mounting bracket (36). It should be understood that such components described above as being associated with control module (12) are merely optional.

Interface lock box (38) mounted to a wall provides tether (40) to lockout port (42) on control module (12). Tether (40) is uniquely terminated and of short length to preclude inadvertent positioning of control module (12) too close to a MRI machine or other machine. In-line enclosure (44) may register tether (40), electrical cable (24) and mechanical cable (26) to their respective ports (42, 28, 30) on control module (12).

Vacuum assist is provided by first vacuum line (46) that connects between control module (12) and outlet port (48) of vacuum canister (50) that catches liquid and solid debris. Tubing kit (52) completes the pneumatic communication between control module (12) and biopsy device (14). In particular, second vacuum line (54) is connected to inlet port (56) of vacuum canister (50). Second vacuum line (54) divides into two vacuum lines (58, 60) that are attached to biopsy device (14). With biopsy device (14) installed in holster portion (32), control module (12) performs a functional check. Saline may be manually injected into biopsy device (14) or otherwise introduced to biopsy device (14), such as to serve as a lubricant and to assist in achieving a vacuum seal and/or for other purposes. Control module (12) actuates a cutter mechanism (not shown) in biopsy device (14), monitoring full travel of a cutter in biopsy device (14) in the present example. Binding in mechanical cable (26) or within biopsy device (14) may optionally monitored with reference to motor force exerted to turn mechanical cable (26) and/or an amount of twist in mechanical cable (26) sensed in comparing rotary speed or position at each end of mechanical cable (26).

Remote keypad (62), which is detachable from holster portion (32), communicates via electrical cable (24) to control panel (12) to enhance clinician control of biopsy device (14) in the present example, especially when controls that would otherwise be on biopsy device (14) itself are not readily accessible after insertion into localization fixture (16) and/or placement of control module (12) is inconveniently remote (e.g., 30 feet away). However, as with other components described herein, remote keypad (62) is merely optional, and may be modified, substituted, supplemented, or omitted as desired. In the present example, aft end thumbwheel (63) on holster portion (32) is also readily accessible after insertion to rotate the side from which a tissue sample is to be taken.

Of course, the above-described control module (12) is merely one example. Any other suitable type of control module (12) and associated components may be used. By way of example only, control module (12) may instead be configured and operable in accordance with the teachings of U.S. Pub. No. 2008/0228103, entitled "Vacuum Timing Algorithm for Biopsy Device," published Sep. 18, 2008, the disclosure of which is incorporated by reference herein. As another merely illustrative example, control module (12) may instead be configured and operable in accordance with the teachings of U.S. patent application Ser. No. 12/337,814, entitled "Control Module Interface for MRI Biopsy Device," filed Dec. 18, 2008, the disclosure of which is incorporated by reference herein. Alternatively, control module (12) may have any other suitable components, features, configurations, functionalities, operability, etc. Other suitable variations of control module (12) and associated components will be apparent to those of ordinary skill in the art in view of the teachings herein.

II. Localization Assembly

Localization assembly (15) of the present example comprises breast coil (18) and localization fixture (16). These components of localization assembly (15) are described further below.

Left and right parallel upper guides (64, 66) of localization framework (68) are laterally adjustably received respectively within left and right parallel upper tracks (70, 72) attached to under side (74) and to each side of a selected breast aperture (76) formed in patient support platform (78) of breast coil (18). Base (80) of breast coil (18) is connected by centerline pillars (82) that are attached to patient support platform (78) between breast apertures (76). Also, a pair of outer vertical support pillars (84, 86) on each side spaced about a respective breast aperture (76) respectively define lateral recess (88) within which localization fixture (16) resides.

It should be appreciated that the patient's breasts hang pendulously respectively into breast apertures (76) within lateral recesses (88) in the present example. For convenience, herein a convention is used for locating a suspicious lesion by Cartesian coordinates within breast tissue referenced to localization fixture (16) and to thereafter selectively position an instrument, such as needle (90) of probe (91) that is engaged to holster portion (32) to form biopsy device (14). Of course, any other type of coordinate system or targeting techniques may be used. To enhance hands-off use of biopsy system (10), especially for repeated re-imaging within the narrow confines of a closed bore MRI machine, biopsy system (10) may also guide obturator (92) encompassed by cannula (94). Depth of insertion is controlled by depth stop device (95) longitudinally positioned on either needle (90) or cannula (94). Alternatively, depth of insertion may be controlled in any other suitable fashion.

This guidance is specifically provided by a lateral fence in the present example, depicted as grid plate (96), which is received within laterally adjustable outer three-sided plate bracket (98) attached below left and right parallel upper guides (64, 66). Similarly, a medial fence with respect to a medial plane of the chest of the patient, depicted as medial plate (100), is received within inner three-sided plate bracket (102) attached below left and right parallel upper guides (64, 66) close to centerline pillars (82) when installed in breast coil (18). To further refine the insertion point of the instrument (e.g., needle (90) of probe (91), obturator/cannula (92, 94), etc.), guide cube (104) may be inserted into grid plate (96).

In the present example, the selected breast is compressed along an inner (medial) side by medial plate (100) and on an outer (lateral) side of the breast by grid plate (96), the latter defining an X-Y plane. The X-axis is vertical (sagittal) with respect to a standing patient and corresponds to a left-to-right axis as viewed by a clinician facing the externally exposed portion of localization fixture (16). Perpendicular to this X-Y plane extending toward the medial side of the breast is the Z-axis, which typically corresponds to the orientation and depth of insertion of needle (90) or obturator/cannula (92, 94) of biopsy device (14). For clarity, the term Z-axis may be used interchangeably with "axis of penetration", although the latter may or may not be orthogonal to the spatial coordinates used to locate an insertion point on the patient. Versions of localization fixture (16) described herein allow a non-orthogonal axis of penetration to the X-Y axis to a lesion at a convenient or clinically beneficial angle.

It should be understood that the above-described localization assembly (15) is merely one example. Any other suitable type of localization assembly (15) may be used, including but not limited to localization assemblies (15) that use a breast coil (18) and/or localization fixture (16) different from those described above. Other suitable components, features, configurations, functionalities, operability, etc. for a localization assembly (15) will be apparent to those of ordinary skill in the art in view of the teachings herein.

III. Biopsy Device

As shown in FIG. 1, one version of biopsy device (14) may comprise holster portion (32) and probe (91). Exemplary holster portion (32) was discussed previously in the above section addressing control module (12). The following paragraphs will discuss probe (91) and associated components and devices in further detail.

Figure 4:
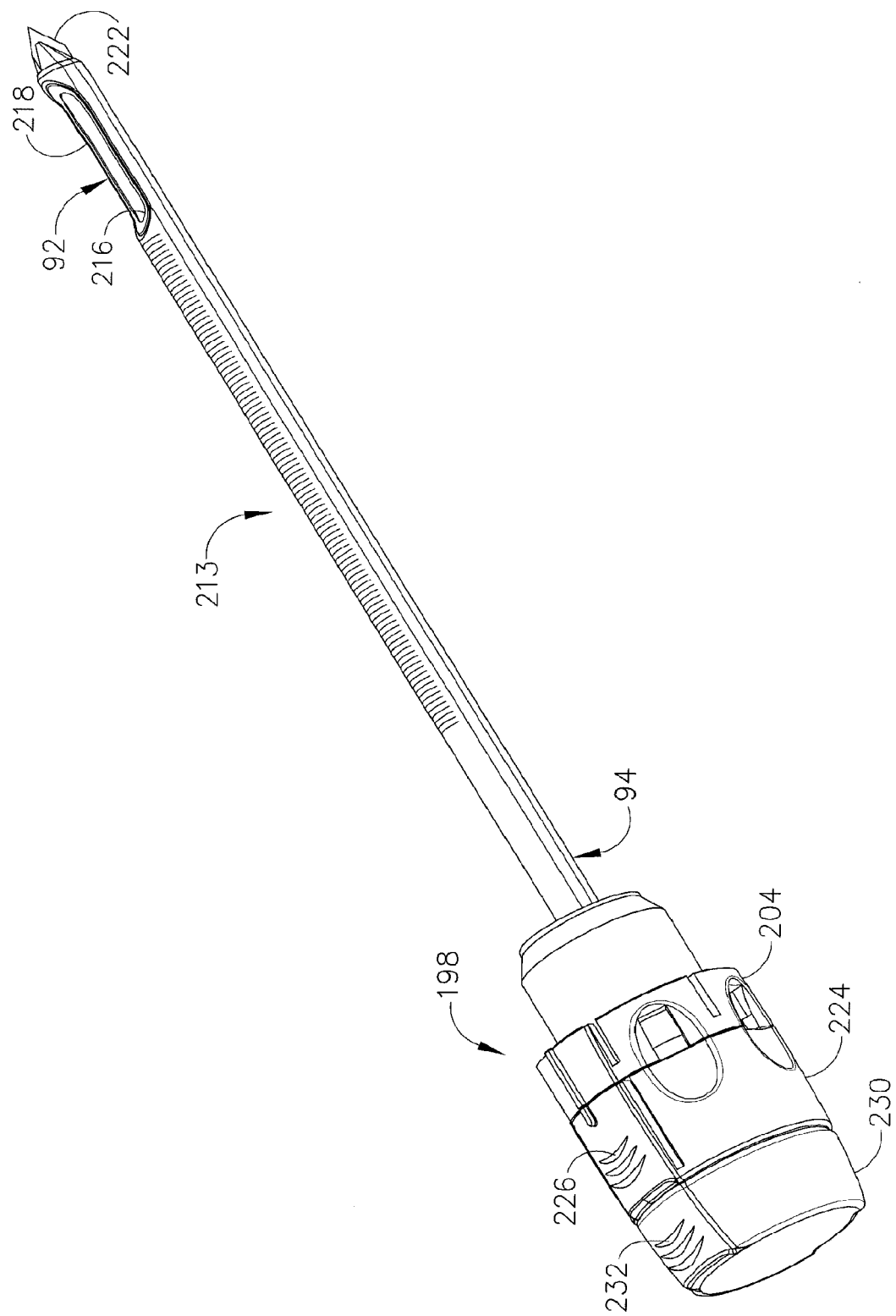
FIG. 4 is a perspective view of the obturator and cannula of the biopsy system of FIG. 1.
Figure 5:
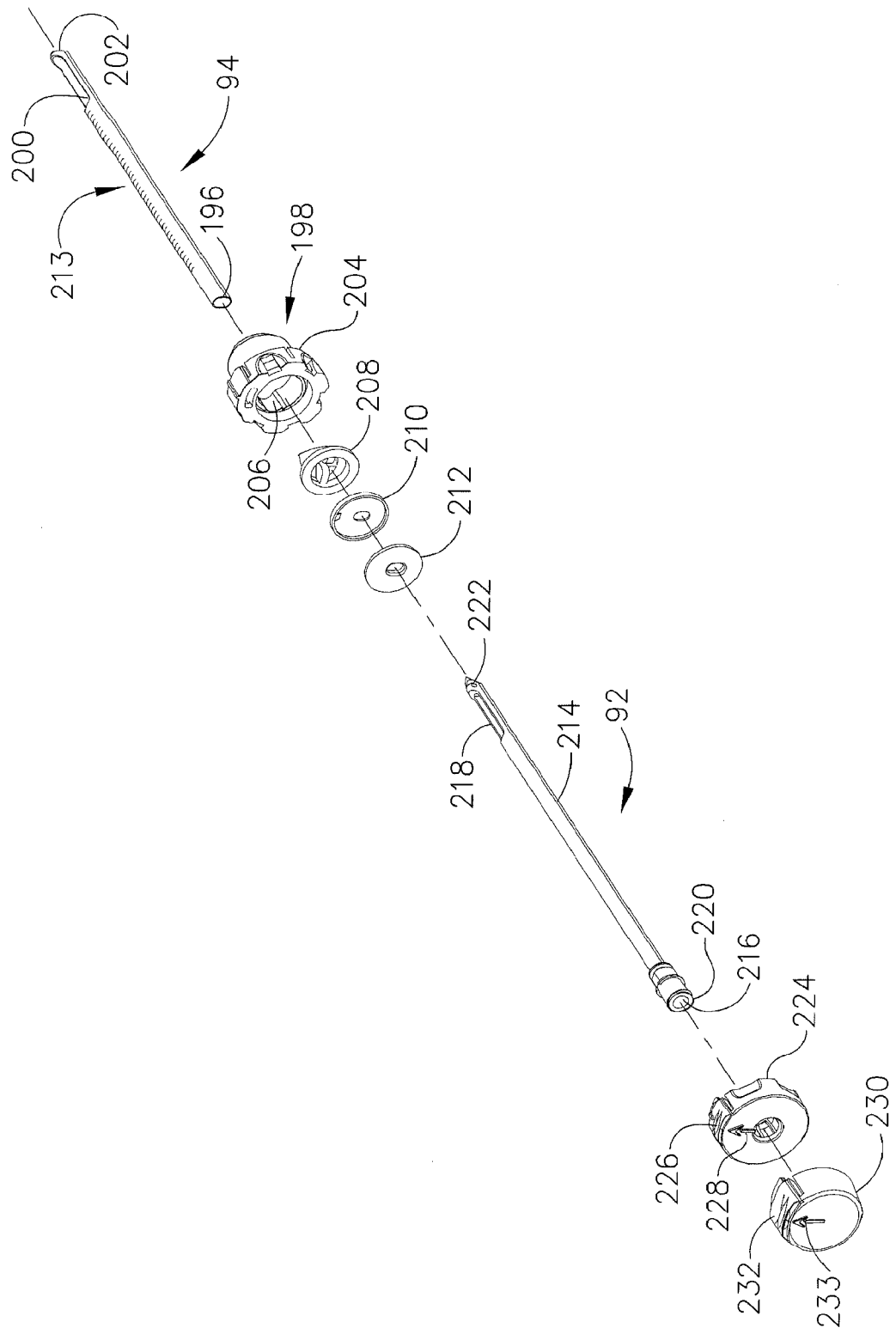
FIG. 5 is an exploded perspective view of the obturator and cannula of FIG. 4.
Figure 7:
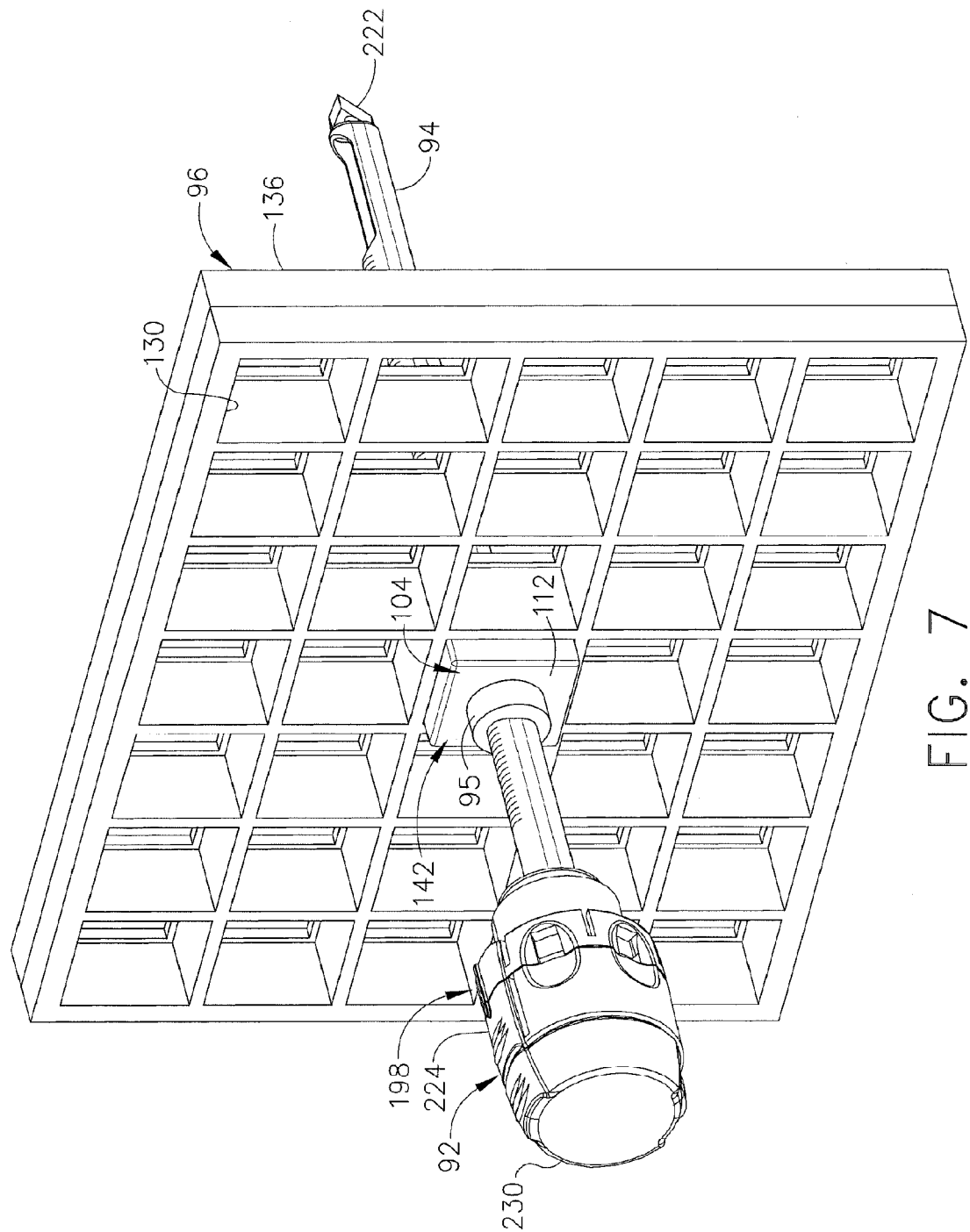
FIG. 7 is a perspective view of the obturator and cannula of FIG. 4 with a depth stop device of FIG. 1 inserted through the guide cube and grid plate of FIG. 6.

In the present example, cannula (94) and obturator (92) are associated with probe (91). In particular, and as shown in FIGS. 4, 5, and 7, obturator (92) is slid into cannula (94) and the combination is guided through guide cube (104) to the biopsy site within the breast tissue. Obturator (92) is then withdrawn from cannula (94), then needle (90) of probe (91) is inserted in cannula (94), and then biopsy device (14) is operated to acquire one or more tissue samples from the breast via needle (90).

Cannula (94) of the present example is proximally attached to cylindrical hub (198) and cannula (94) includes lumen (196) and lateral aperture (200) proximate to open distal end (202). Cylindrical hub (198) has exteriorly presented thumbwheel (204) for rotating lateral aperture (200). Cylindrical hub (198) has interior recess (206) that encompasses duckbill seal (208), wiper seal (210) and seal retainer (212) to provide a fluid seal when lumen (196) is empty and for sealing to inserted obturator (92). Longitudinally spaced measurement indicia (213) along an outer surface of cannula (94) visually, and perhaps physically, provide a means to locate depth stop device (95) of FIG. 1.

Obturator (92) of the present example incorporates a number of components with corresponding features. Hollow shaft (214) includes fluid lumen (216) that communicates between imageable side notch (218) and proximal port (220). Hollow shaft (214) is longitudinally sized to extend, when fully engaged with cannula (94), piercing tip (222) out of distal end (202) of cannula (94). Obturator thumbwheel cap (224) encompasses proximal port (220) and includes locking feature (226), which includes visible angle indicator (228), that engages cannula thumbwheel (204) to ensure that imageable side notch (218) is registered to lateral aperture (200) in cannula (94). Obturator seal cap (230) may be engaged proximally into obturator thumbwheel cap (224) to close fluid lumen (216). Obturator seal cap (230) of the present example includes locking or locating feature (232) that includes visible angle indicator (233) that corresponds with visible angle indicator (228) on obturator thumbwheel cap (224), which may be fashioned from either a rigid, soft, or elastomeric material. In FIG. 7, guide cube (104) has guided obturator (92) and cannula (94) through grid plate (96).

While obturator (92) of the present example is hollow, it should be understood that obturator (92) may alternatively have a substantially solid interior, such that obturator (92) does not define an interior lumen. In addition, obturator (92) may lack side notch (218) in some versions. Other suitable components, features, configurations, functionalities, operability, etc. for an obturator (92) will be apparent to those of ordinary skill in the art in view of the teachings herein. Likewise, cannula (94) may be varied in a number of ways. For instance, in some other versions, cannula (94) has a closed distal end (202). As another merely illustrative example, cannula (94) may have a closed piercing tip (222) instead of obturator (92) having piercing tip (222). In some such versions, obturator (92) may simply have a blunt distal end; or the distal end of obturator (92) may have any other suitable structures, features, or configurations. Other suitable components, features, configurations, functionalities, operability, etc. for a cannula (94) will be apparent to those of ordinary skill in the art in view of the teachings herein. Furthermore, in some versions, one or both of obturator (92) or cannula (94) may be omitted altogether. For instance, needle (90) of probe (91) may be directly inserted into a guide cube (104), without being inserted into guide cube (104) via cannula (94).

Another component that may be used with probe (91) (or needle (90)) is depth stop (95). Depth stop may be of any suitable configuration that is operable to prevent cannula (94) and obturator (92) (or needle (90)) from being inserted further than desired. For instance, depth stop (95) may be positioned on the exterior of cannula (94) (or needle (90)), and may be configured to restrict the extent to which cannula (94) is inserted into a guide cube. It should be understood that such restriction by depth stop (95) may further provide a limit on the depth to which the combination of cannula (94) and obturator (92) (or needle (90)) may be inserted into the patient's breast. Furthermore, it should be understood that such restriction may establish the depth within the patient's breast at which biopsy device (14) acquires one or more tissue samples after obturator (92) has been withdrawn from cannula (94) and needle (90) has been inserted in cannula (94). Exemplary depth stops (95) that may be used with biopsy system (10) are described in U.S. Pub. No. 2007/0255168, entitled "Grid and Rotatable Cube Guide Localization Fixture for Biopsy Device," published Nov. 1, 2007, and incorporated by reference herein as mentioned previously.

In the present example, and as noted above, biopsy device (14) includes a needle (90) that may be inserted into cannula (94) after the combination of cannula (94) and obturator (92) has been inserted to a desired location within a patient's breast and after obturator (92) has been removed from cannula (94). Needle (90) of the present example comprises a lateral aperture (not shown) that is configured to substantially align with lateral aperture (200) of cannula (94) when needle (90) is inserted into lumen (196) of cannula (94). Probe (91) of the present example further comprises a rotating and translating cutter (not shown), which is driven by components in holster (32), and which is operable to sever tissue protruding through lateral aperture (200) of cannula (94) and the lateral aperture of needle (90). Severed tissue samples may be retrieved from biopsy device (14) in any suitable fashion.

By way of example only, biopsy device (14) may be configured and operable in accordance with the teachings of U.S. Pub. No. 2008/0228103, entitled "Vacuum Timing Algorithm For Biopsy Device," published Sep. 18, 2008, the disclosure of which is incorporated by reference herein. As another merely illustrative example, biopsy device (14) may be configured and operable in accordance with the teachings of U.S. patent application Ser. No. 12/337,874, entitled "Mechanical Tissue Sample Holder Indexing Device," filed Dec. 18, 2008, the disclosure of which is incorporated by reference herein. As another merely illustrative example, biopsy device (14) may be configured and operable in accordance with the teachings of U.S. patent application Ser. No. 12/337,674, entitled "Biopsy Device with Sliding Cutter Cover," filed Dec. 18, 2008, the disclosure of which is incorporated by reference herein. By way of example only, cannula (94) may be replaced with any of the detachable needles described in U.S. patent application Ser. No. 12/337,674, entitled "Biopsy Device with Sliding Cutter Cover." As another merely illustrative example, biopsy device (14) may be configured and operable in accordance with the teachings of U.S. patent application Ser. No. 12/337,911, entitled "Biopsy Device with Discrete Tissue Chambers," filed Dec. 18, 2008, the disclosure of which is incorporated by reference herein. As another merely illustrative example, biopsy device (14) may be configured and operable in accordance with the teachings of U.S. patent application Ser. No. 12/337,942, entitled "Biopsy Device with Central Thumbwheel," filed Dec. 18, 2008, the disclosure of which is incorporated by reference herein. Alternatively, biopsy device (14) may have any other suitable components, features, configurations, functionalities, operability, etc. Other suitable variations of biopsy device (14) and associated components will be apparent to those of ordinary skill in the art in view of the teachings herein IV. Guide Cubes Guide cubes described below are generally adapted for use with a localization assembly (15) as described above. Numerous features of merely exemplary guide cubes will be discussed in the paragraphs that follow.

A. Guide Cubes Generally

In some versions, guide cubes may comprise a body defined by one or more edges and faces. The body may include one or more guide holes or other types of passages that extend between faces of the guide cube and that may be used to guide an instrument such as a biopsy device (14) or a portion of a biopsy device (14) (e.g., needle (90) of biopsy device (14), a combination of cannula (94) and obturator (92), etc.). Guide cubes may be rotatable about one, two, or three axes to position the one or more guide holes or passages of the guide cube into a desired position.

Figure 8:
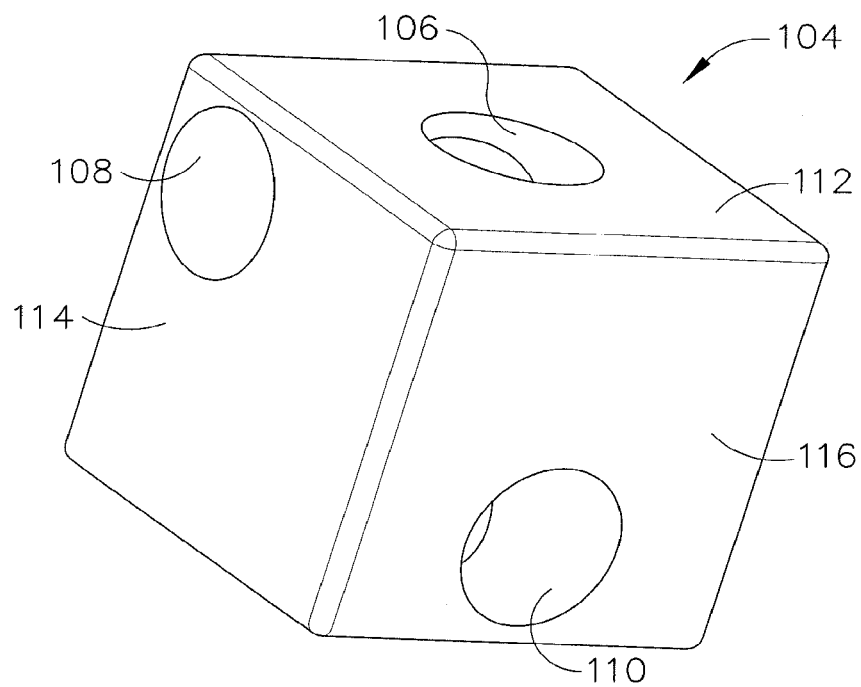
FIG. 8 is a perspective view of the guide cube of the biopsy system of FIG. 1.
Figure 9:
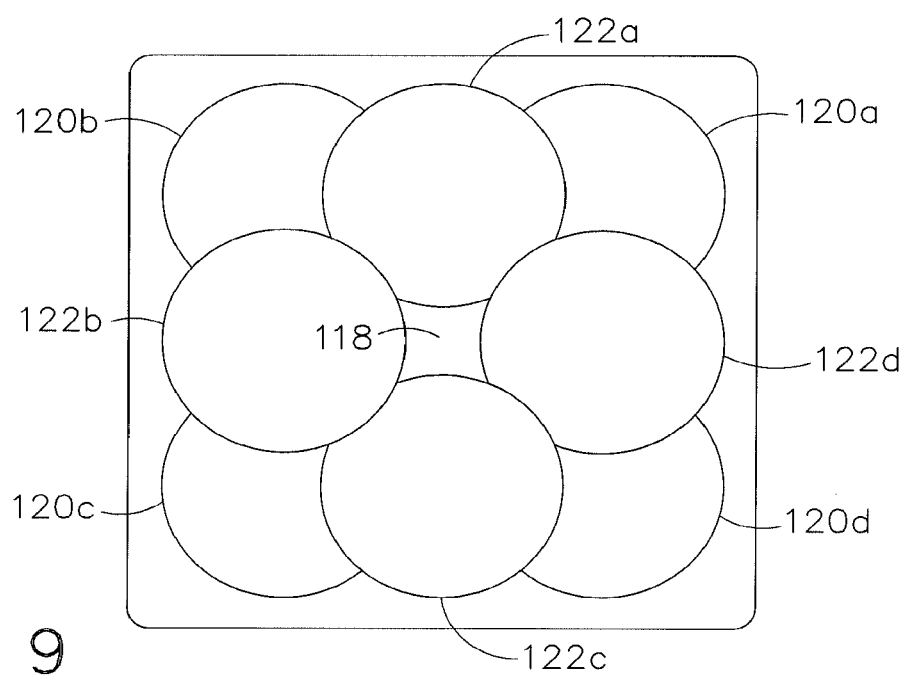
FIG. 9 is a diagram of nine guide positions achievable by rotating the guide cube of FIG. 8.

Referring now to FIG. 8, guide cube (104), includes central guide hole (106), corner guide hole (108), and off-center guide hole (110) that pass orthogonally to one another between respective opposite pairs of faces (112, 114, 116). By selectively rotating guide cube (104) in two axes, one pair of faces (112, 114, 116) may be proximally aligned to an unturned position and then the selected proximal face (112, 114, 116) optionally rotated a quarter turn, half turn, or three-quarter turn. Thereby, one of nine guide positions (118, 120a-120d, 122a-122d) may be proximally exposed as depicted in FIG. 9. More specifically, central guide hole (106) may provide for guide position (118), corner guide hole (108) may provide for guide positions (120a-120d), and off-center guide hole (110) may provide for guide positions (122a-122d).

Figure 6:
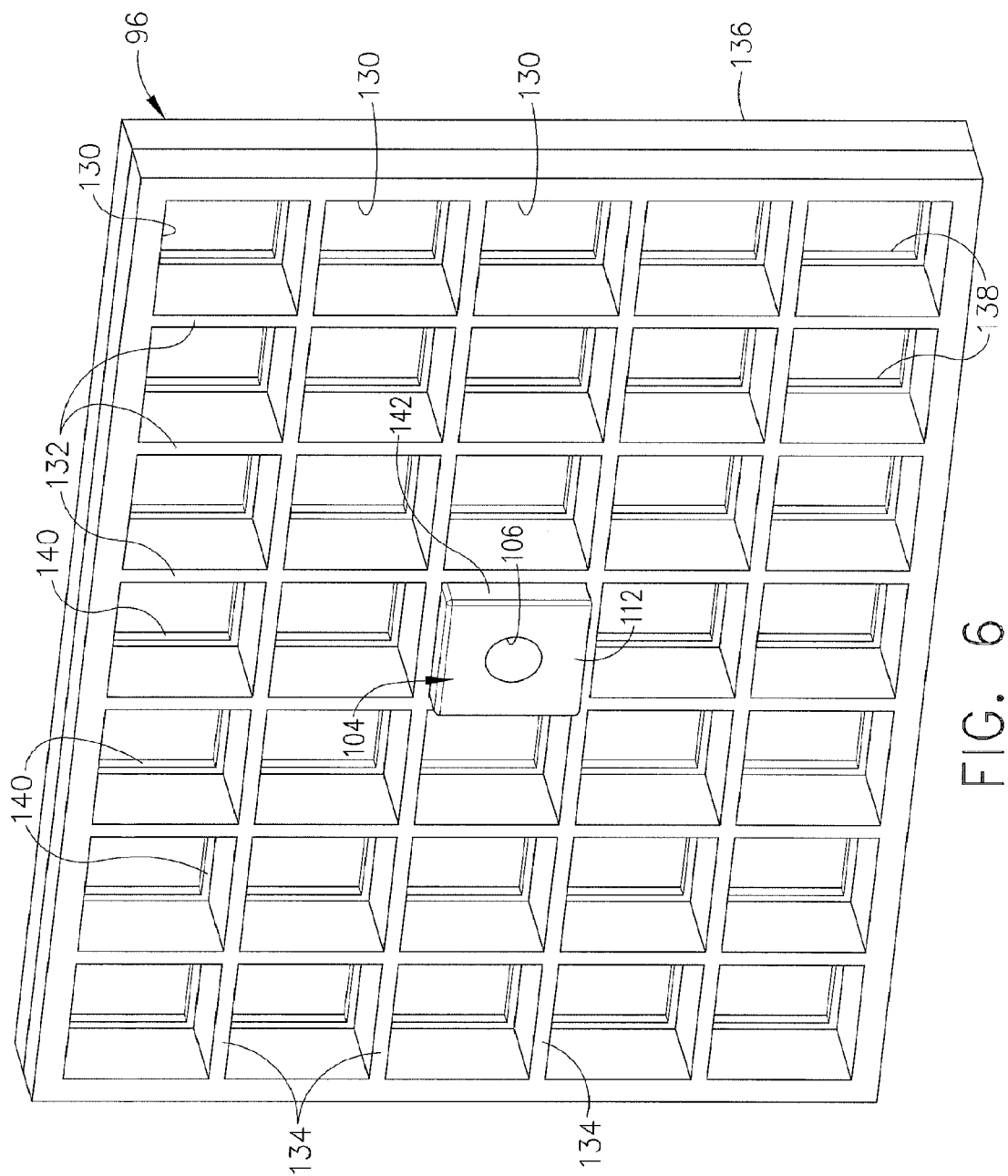
FIG. 6 is a perspective view of the guide cube inserted into the grid plate of the localization assembly of FIG. 1.

In FIG. 6, two-axis rotatable guide cube (104) is sized for insertion from a proximal side into one of a plurality of square recesses (130) in grid plate (96), which are formed by intersecting vertical bars (132) and horizontal bars (134). Guide cube (104) is prevented from passing through grid plate (96) by backing substrate (136) attached to a front face of grid plate (96). Backing substrate (136) includes respective square opening (138) centered within each square recess (130), forming lip (140) sufficient to capture the front face of guide cube (104), but not so large as to obstruct guide holes (104, 106, 108). The depth of square recesses (130) is less than guide cube (104), thereby exposing a proximal portion (142) of guide cube (104) for seizing and extraction from grid plate (96). It will be appreciated by those of ordinary skill in the art based on the teachings herein that backing substrate (136) of grid plate (96) may be omitted altogether in some versions. In some such versions without backing substrate (136) other features of a guide cube, as will be discussed in more detail below, may be used to securely and removably fit a guide cube within a grid plate. However, such other features may also be used in combination with a grid plate having backing substrate (136), such as grid plate (96), instead of partially or wholly omitting backing substrate (136).

B. Self-Grounding Guide Cubes

Figure 10:
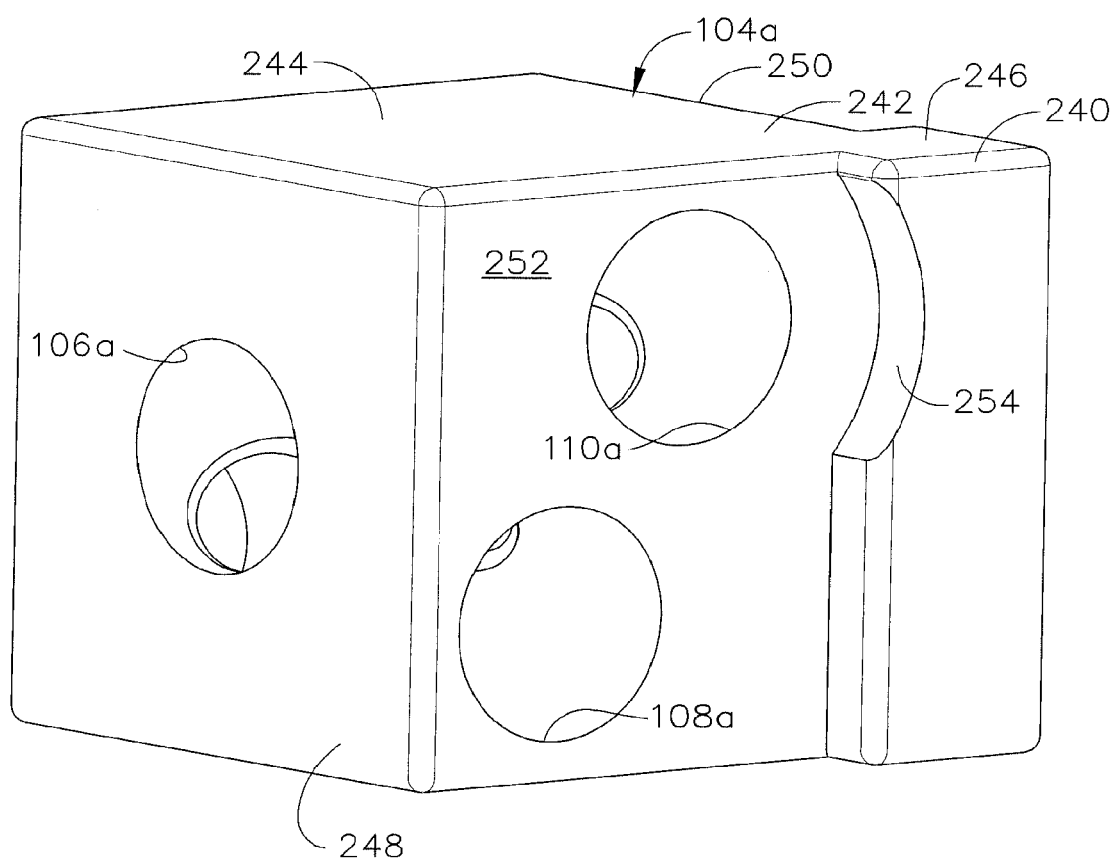
FIG. 10 is a perspective view of another guide cube for the biopsy system of FIG. 1 with a self-grounding feature.
Figure 11:
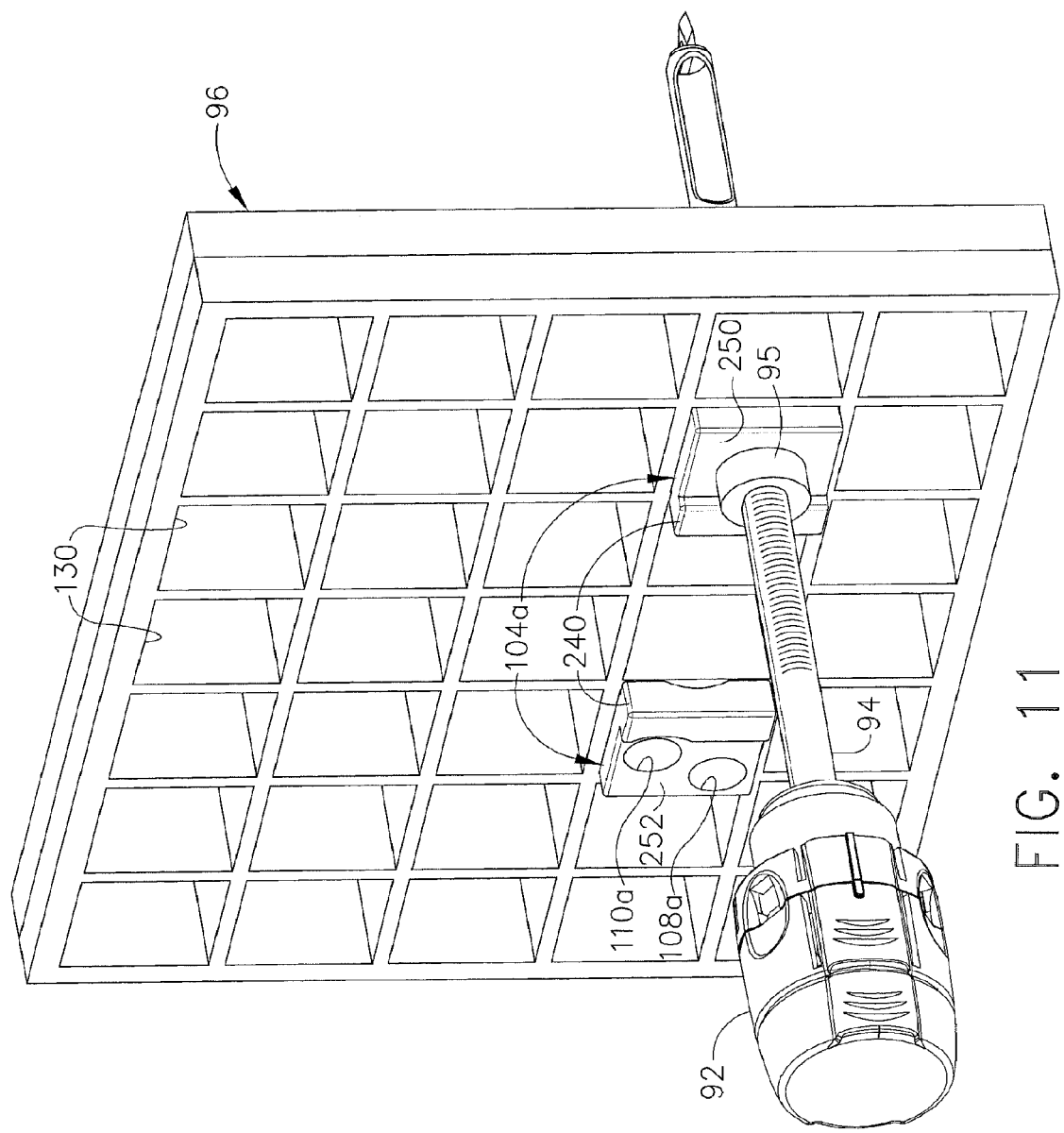
FIG. 11 is a perspective view of the obturator and cannula of FIG. 1 inserted into one of two guide cubes of FIG. 10 inserted into the grid plate of FIG. 1.

In FIG. 10, guide cube (104a) has self-grounding by means of added rectangular prism (240) which has a shared edge with cubic portion (242) of guide cube (104a). When viewed orthogonally to the shared cube edge, larger square face (244) of cubic portion (242) overlaps with smaller square face (246) of rectangular prism (240). As shown in FIG. 11, rectangular prism (240) allows proximal exposure of one of two adjacent faces (250, 252) of guide cube (104a) and then turning each to one of four quarter-turn rotational positions. In the illustrative version, first face (250) has central guide hole (106a) and second face (252) has corner guide hole (108a), and off-center guide hole (110a). Radial recess (254) is formed in rectangular prism (240) to allow grounding of depth stop device (95) against face (252) when off-center guide hole (110a) is used.

Figure 12:
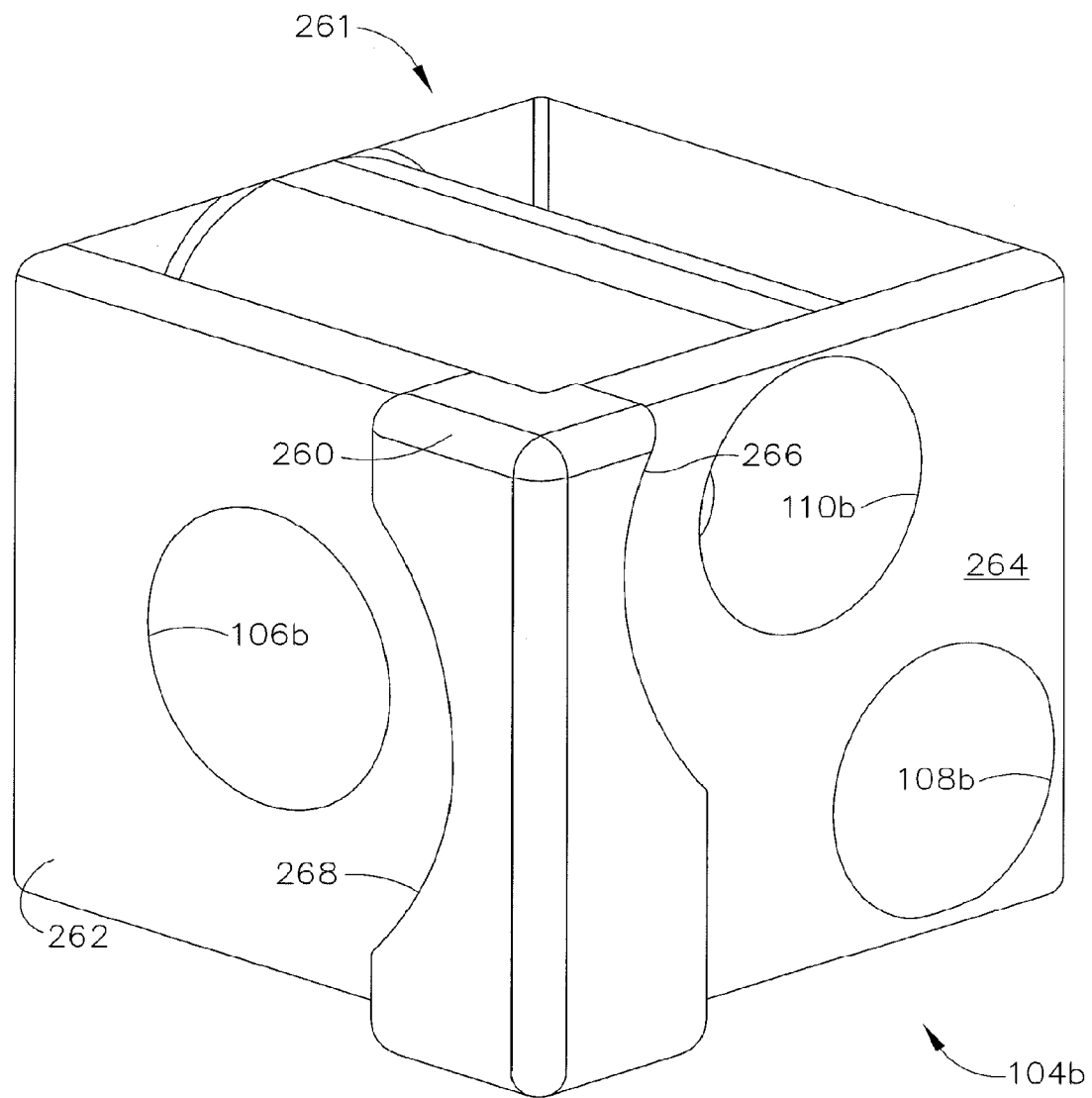
FIG. 12 is a perspective view of another guide cube having an open top and bottom with another self-grounding feature.

In FIG. 12, guide cube (104b) has self-grounding by means of added rectangular prism (260) that protrudes from two faces (262, 264) of guide cube (104b). Rectangular prism (260) allows proximal exposure of one of two adjacent faces (262, 264) of guide cube (104b) and then turning each to one of four quarter-turn rotational positions. In the illustrative version, first face (262) has central guide hole (106b) and second face (264) has corner guide hole (108b) and off-center guide hole (110b). First radial recess (266) is formed in rectangular prism (260) to allow grounding of depth stop device (95) against face (264) when off-center guide hole (110b) is used. Second radial recess (268) is formed in rectangular prism (260) to allow grounding of depth stop device (95) against face (262) when central guide hole (106b) is used. As discussed in greater detail below, guide cube (104b) may have open top (261) and/or an open bottom (not shown) defined by the faces of guide cube (104b) as depicted in the illustrated version.

Figure 13:
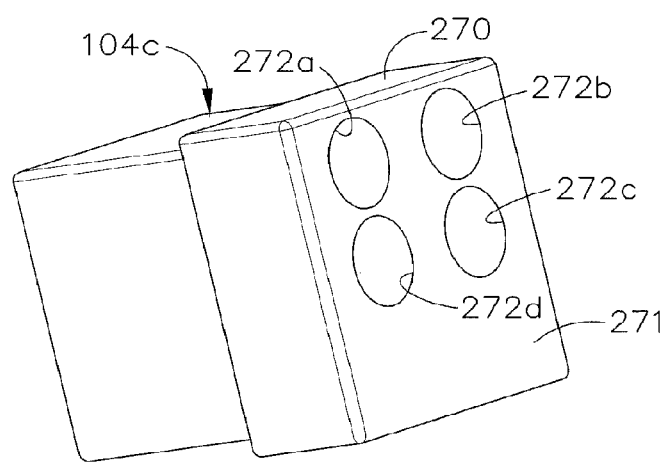
FIG. 13 is a rear perspective view of another guide cube with another self-grounding feature.
Figure 14:
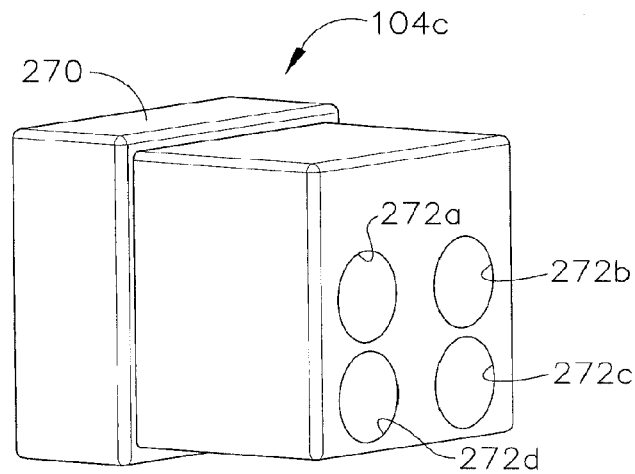
FIG. 14 is a front perspective view of the guide cube of FIG. 13.
Figure 15:
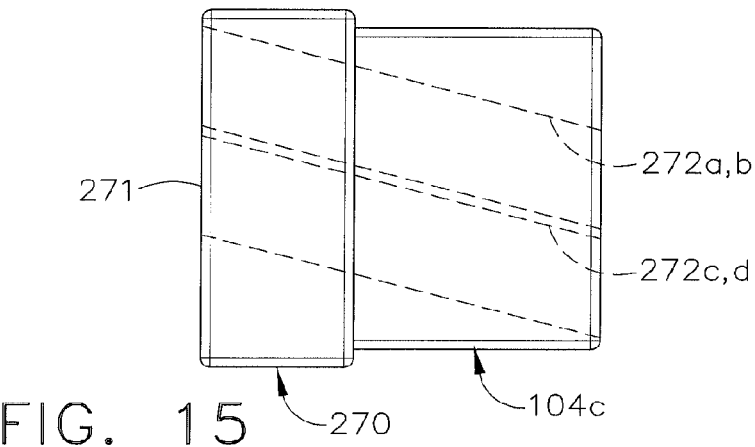
FIG. 15 is a right side view of the guide cube of FIG. 13 with angled, parallel guide holes depicted in phantom.

In FIGS. 13-15, guide cube (104c) has proximal enlarged hat portion (270) about proximal face (271) that grounds against selected square recess (130), such as in grid plate (96), and allows rotation about one axis to one of four quarter-turn positions. Four angled guide holes (272a, 272b, 272c, 272d) allow accessing not only an increased number of insertion points within selected square recess (130) but also a desired angle of penetration rather than being constrained to a perpendicular insertion. It will be appreciated based on the teachings herein that while angled guide holes may be used in some versions, orthogonal guide holes may be used instead of or in addition to angled guide holes in other versions.

C. Elastomeric Edges

Figure 16:
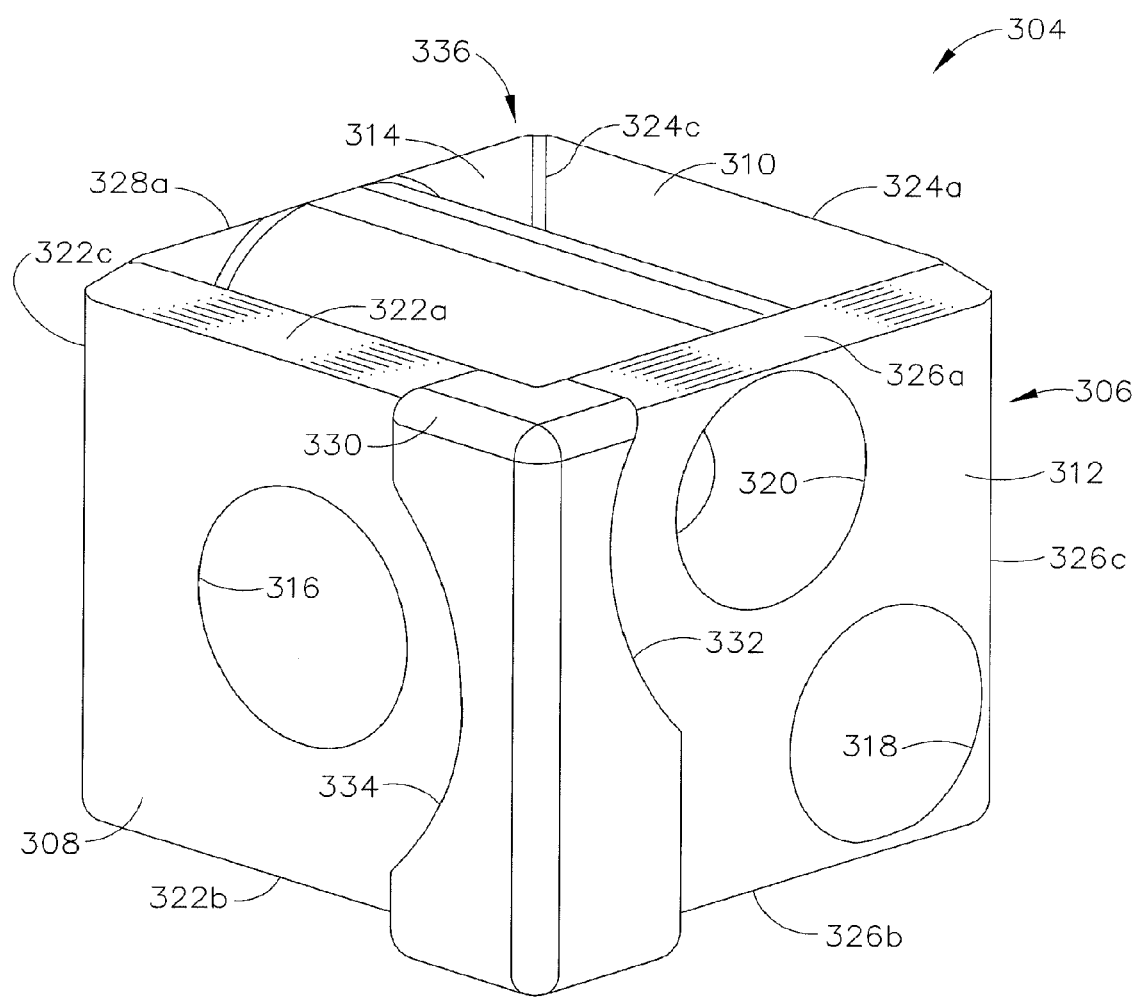
FIG. 16 is a front perspective view of another guide cube having elastomeric edges.
Figure 17:
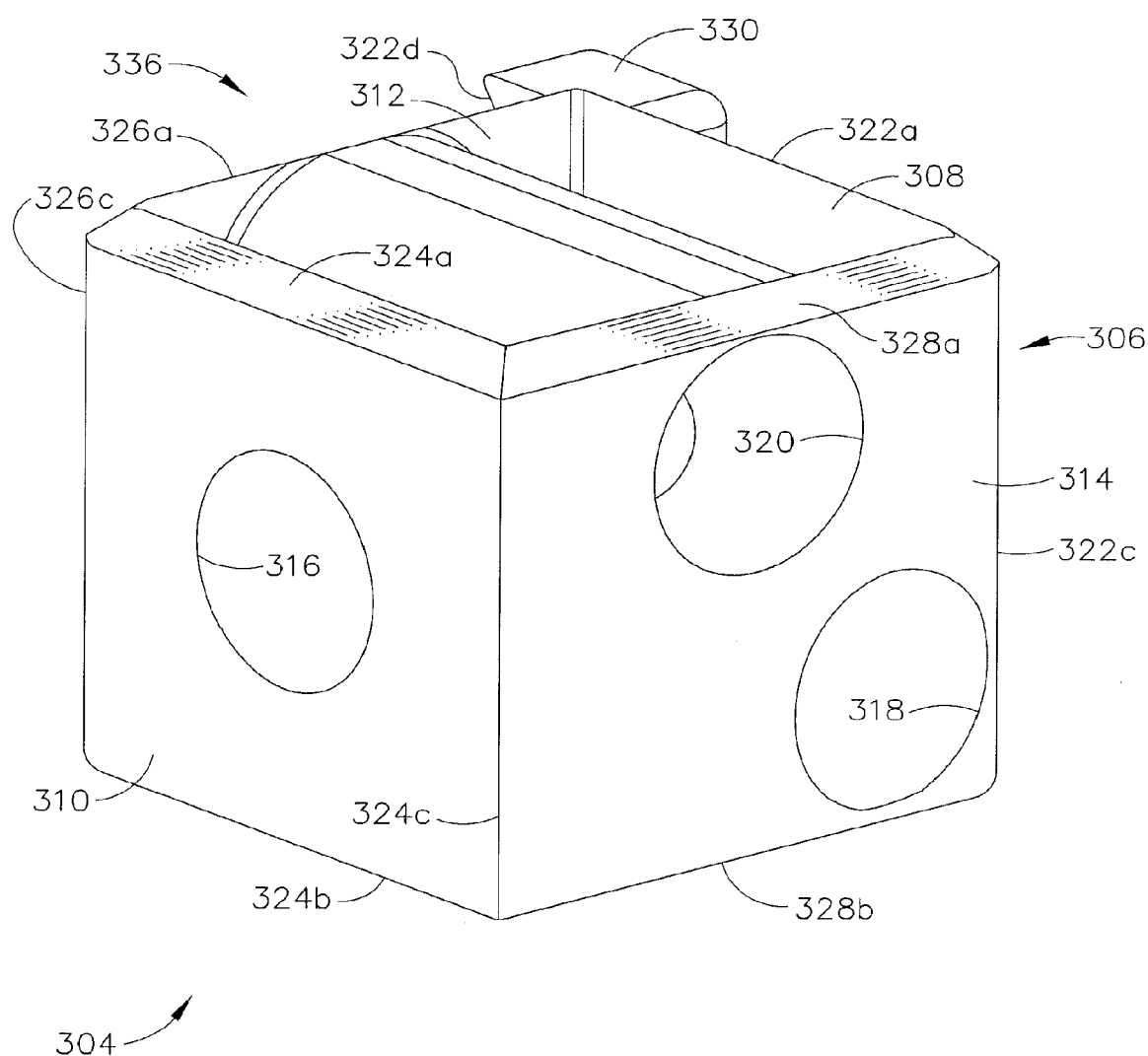
FIG. 17 is a rear perspective view of the guide cube of FIG. 16.

In FIGS. 16 and 17, guide cube (304) includes body (306) defined by four faces (308, 310, 312, 314). Faces (308, 310, 312, 314) include two sets of opposing faces, as shown in the illustrated version where face (308) and face (310) are opposing and likewise face (312) and face (314) are opposing. Guide cube (304) has guide holes (316, 318, 320) passing through guide cube (304). Guide holes (316, 318, 320) have corresponding openings in a set of opposing faces thereby providing access via a passageway from one side of guide cube (304) to the other side. It should be appreciated that guide holes may be configured to share a common opening in a face in some versions. As shown in the illustrated version, faces (308, 310) include central guide hole (316), while faces (312, 314) include corner guide hole (318) and off-center guide hole (320). However, it should be understood that faces (308, 310, 312, 314) may each have any suitable number of guide holes in any suitable positioning or arrangements, and that any suitable number of passages may be provided through guide cube (304).

Each face (308, 310, 312, 314) of guide cube (304) may be defined by edges. In such a configuration, it will be appreciated that some faces (308, 310, 312, 314) may share one or more common edges. For instance, face (308) may be defined by edges (322a-322d). Face (312) may be defined by edges (326a-326c, 322d). Face (310) may be defined by edges (324a-324c, 326c). Face (314) may be defined by edges (328a, 328b, 322c, 324c). It should be further appreciated that faces (308, 310, 312, 314) may be configured such that each does not share common edges, but rather the edges of adjacent faces abut one another forming the edges (322a-322d, 324a-324c, 326a-326c, 328a-328b) of guide cube (304). For instance, faces (308, 310, 312, 314) may be initially formed separately, such as by being formed as separate plates, with each plate having its own four edges, and with the separate plates being joined together to form guide cube (304), etc.).

As shown in FIG. 16, at least a portion of edges (322a-322d, 324a-324c, 326a-326c, 328a-328b) of guide cube (304) may be comprised of or fitted with elastomeric material. In FIG. 16, edges (322a, 324a, 326a, 328a, 322b, 324b, 326b, and 328b) are comprised of elastomeric material. This provides guide cube (304) with the opposing edges of four faces (308, 310, 312, 314) having an elastomeric edge.

Based on the teachings herein, it will be appreciated that other guide cube versions may arrange the elastomeric edges in any suitable configuration. For instance in other versions all edges of a guide cube may have elastomeric edges. Any arrangement of elastomeric edges that aids in improved fit of a guide cube with a grid plate may be suitable.

Guide cube (304) may further be rotatable in two axes with self-grounding by means of rectangular prism (330) that protrudes from two faces (308, 312) of guide cube (304). Rectangular prism (330) allows proximal exposure of one of two adjacent faces (308, 312) of guide cube (304) and then turning each to one of four quarter-turn rotational positions. In the illustrative version, first radial recess (332) is formed in rectangular prism (330) to allow grounding of depth stop device (95) against face (312) when off-center guide hole (320) is used. Second radial recess (334) is formed in rectangular prism (330) to allow grounding of depth stop device (95) against face (308) when central guide hole (316) is used.

Guide cube (304) may have open top (336) and/or an open bottom (not shown) defined by faces (308, 310, 312, 314) of guide cube (304) as depicted in the illustrated version. Open top (336) and open bottom (not shown) may provide void volume within guide cube (304), and depending on the rigidity of body (306), body portion (306) may flex to some degree thereby permitting better fit within a grid plate or more compatible fit within various grid plates. Alternatively, guide cube (304) may have a closed top and/or bottom. Similarly, aside from the passageways provided between guide holes (316, 318, 320), the interior of guide cube (304) may be substantially hollow or substantially solid, as desired.

Based on the teachings herein, those of ordinary skill in the art will appreciate that several elastomeric materials may be suitable for use with guide cube (304). By way of example only, suitable elastomeric materials may include thermosetting plastics that may require vulcanization, thermoplastic elastomers (e.g. Santoprene™ among others), natural rubber, synthetic rubbers (e.g. ethylene propylene diene M-class—EPDM—among others), and other polymers having suitable elastic properties.

Creating a guide cube having elastomeric edges may be accomplished in a variety of ways. For example, in creating a guide cube such as guide cube (304) that has elastomeric edges (322a, 324a, 326a, 328a, 322b, 324b, 326b, 328b), in some versions a multi-shot molding process may be used where body (306) of guide cube (304) may be molded from a first material, e.g. a non-elastomeric material, and the elastomeric edges may be molded from a second material, e.g. an elastic material as described above or otherwise. In some other versions, elastomeric edges (322a, 324a, 326a, 328a, 322b, 324b, 326b, 328b) may be molded or extruded separate from body (306) and then coupled with body (306) by mechanical fastening, chemical adhesive, or other suitable bonding or coupling techniques.

Based on the teachings herein, those of ordinary skill in the art will appreciate that the configuration of the elastomeric edges, the type of elastomeric material used for the edges, the application process used to apply the elastomeric material to the edges, and other factors may influence whether or not a specific elastomeric edge design and material are suitable. Those of ordinary skill in the art, based on the teachings herein, will further appreciate that suitable designs for a guide cube having at least one elastomeric edge may create a secure interference between a grid plate and guide cube without significantly increasing the force required to insert or remove the guide cube from the grid plate. Accordingly, guide cube (304) of the present example may fit in various types of grid plates having grid openings or recesses of various sizes or configurations. It should also be understood that, in some settings, the presence of elastomeric material on edges (322a, 324a, 326a, 328a, 322b, 324b, 326b, 328b) may provide sufficient friction with a grid plate to reduce the likelihood that guide cube (304) will undesirably fall out of the grid plate. In addition, other suitable features, configurations, components, functionalities, operability, and variations of guide cube (304) will be apparent to those of ordinary skill in the art in view of the teachings herein.

D. Elastomeric Body

FIGS. 18-21 depict other versions of guide cubes that comprise an elastomeric body that may compress to fit with multiple grid plates having openings that may vary in shape and/or size from grid plate to grid plate, or even within a single grid plate. Those of ordinary skill in the art will appreciate, based on the teachings herein, that the elastomeric nature of the body in these examples may greatly increase the compatibility of the guide cubes for use with various grid plates. In addition to, or separately from the elastomeric body compressing to fit with multiple grid plates, FIGS. 18-21 also depict versions of guide cubes having expanding access ports. The expanding access ports may be defined by or surrounded by an elastomeric body or a portion of an elastomeric body that allows expansion of the access ports when a portion of a biopsy device is inserted into an access port. While the concept of an elastomeric body is described in greater detail below with reference to examples depicted in FIGS. 18-21, it should be understand that the concept may alternatively be applied to any guide cube described herein and to variations of such guide cubes. Accordingly, the concept of an elastomeric body is not necessarily limited to the examples depicted in FIGS. 18-21 and described below.

Figure 18:
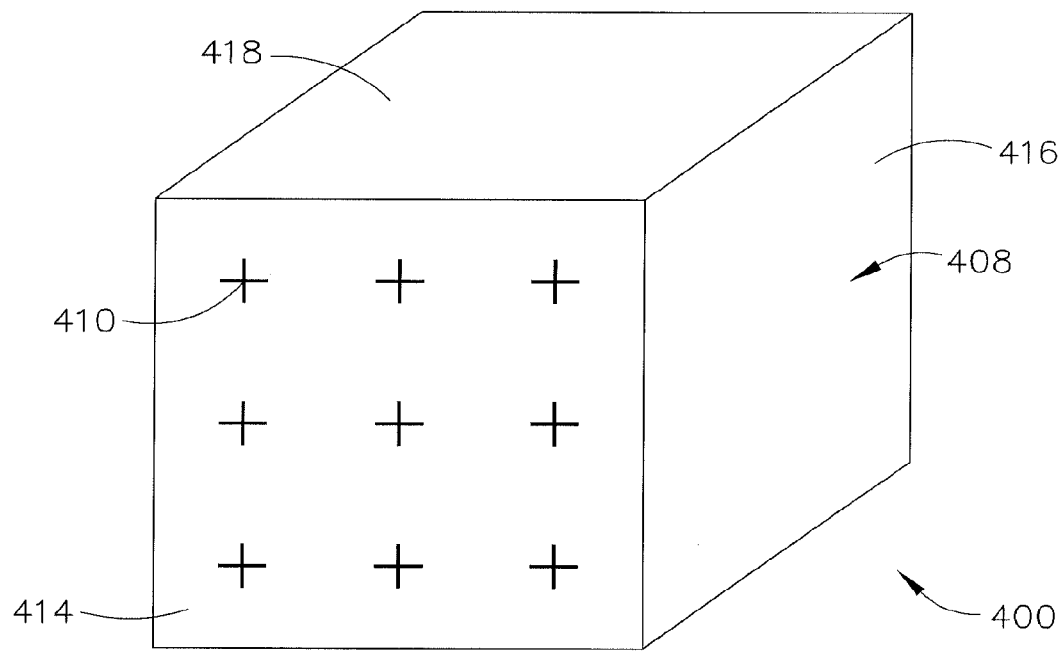
FIG. 18 is a perspective view of another guide cube having an elastomeric body and nine expanding access slits for receiving a portion of a biopsy device.

Referring now to FIG. 18, guide cube (400) has elastomeric body (408) having nine access slits (410) for receiving probe (91) and/or other components of biopsy device (14). Of course, any other suitable number of access slits (410) may be provided, including more than nine or less than nine. It should also be understood that slits (410) may be of various lengths and/or widths, etc. The nature of elastomeric body (408) allows body (408) to compress when fitted within a smaller opening in a grid plate. When in a compressed state and inserted into an opening in a grid plate, the elastomeric body (408) provides a force against inner wall portions of the grid plate that define the grid plate opening, such that the guide cube (400) is securely held in position. As discussed previously, a portion of guide cube (400) may protrude from the proximal side of the grid plate such that guide cube (400) remains accessible to the user. To remove guide cube (400), the user may grasp the protruding portion of guide cube (400), provide further compressive force to reduce the size of guide cube (400), and withdrawal guide cube (400) from the grid plate opening.

Guide cube (400) further may comprise access slits (410) that extend from first face (414) through guide cube (400) to opposing face (not shown), to provide a passageway between opposing faces. In the illustrated version, biopsy device (14) may be used with any of selected access slits (410) with or without the need to rotate guide cube (400). In use, when the combination of cannula (94) and obturator (92) (or needle (90)) is inserted into a selected access slit (410), the nature of elastomeric body (408) surrounding access slit (410) is such that elastomeric body (408) may compresses to accommodate the volume of the introduced combination of cannula (94) and obturator (92) (or needle (90)). It should be understood that entire length of cannula (94) (or needle (90)) need not be inserted into a guide hole or access slits (410) and that in some versions only a portion of the length of cannula (94) (or needle (90)) may be inserted into the guide holes or access slits (410). In some versions, nearby access slits (410) or guide holes that do not receive the combination of cannula (94) and obturator (92) (or needle (90)) may compress upon the insertion of the combination of cannula (94) and obturator (92) (or needle (90)) into the selected access slit (410). In some versions, where guide cube (400) is inserted into a grid plate opening, the insertion of the combination of cannula (94) and obturator (92) (or needle (90)) into access slit (410) causes elastomeric body (408) to exert further force against the walls of the grid plate that define the grid plate opening. It will be appreciated based on the teachings herein that elastomeric body (408) and access slits (410) may work together to provide a sufficient outward force from guide cube (400) to the walls defining the grid plate opening such that guide cube (400) fits within the grid plate opening securely both during insertion of the combination of cannula (94) and obturator (92) (or needle (90)) through access slit (410) and during withdrawal of cannula (94) (or needle (90)) through access slit (410).

Figure 19:
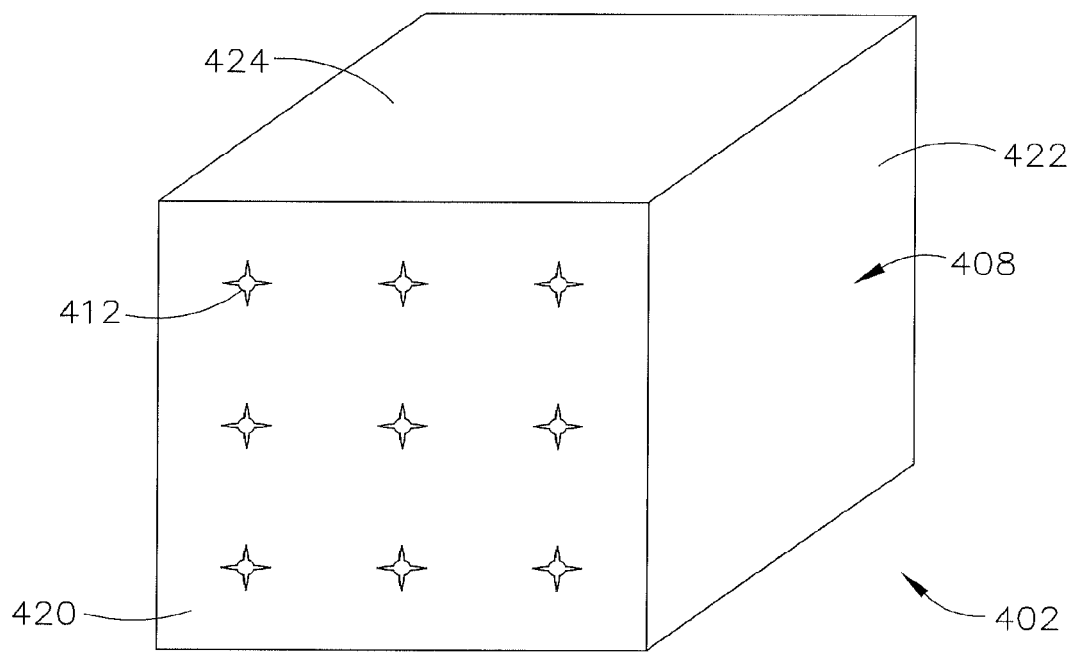
FIG. 19 is a perspective view of another guide cube having an elastomeric body and nine expanding access star-shaped openings for receiving a portion of a biopsy device.

Referring now to FIG. 19, guide cube (402) has elastomeric body (408) having nine access star-shaped openings (412) for receiving probe (91) and/or other components of biopsy device (14). Of course, any other suitable number of openings (412) may be provided, including more than nine or less than nine. Similarly, openings (412) need not be star-shaped, and can have any other suitable shape. For instance, openings (412) may include any type of undersized access openings with any number of slits around (e.g., extending radially outwardly relative to) the perimeter of each opening. "Undersized" in some settings may mean that the diameter of a relaxed opening (412) (e.g., one without a cannula (94) (or needle (90)) inserted in it) is less than the diameter of a cannula (94) (or needle (90)). The nature of elastomeric body (408) in the present example allows body (408) to compress when fitted within a smaller opening in a grid plate. When in a compressed state and inserted into an opening in a grid plate, the elastomeric body (408) provides a force against inner wall portions of the grid plate that define the grid plate opening, such that the guide cube (402) is securely held in position. As discussed previously, a portion of guide cube (402) may protrude from the proximal side of the grid plate such that guide cube (402) remains accessible to the user. To remove guide cube (402), the user may grasp the protruding portion of guide cube (402), provide further compressive force to reduce the size of guide cube (402), and withdrawal guide cube (402) from the grid plate opening.

Guide cube (402) further may comprise access star-shaped openings (412) that extend from first face (420) through guide cube (402) to opposing face (not shown), to provide a passageway between opposing faces. In the illustrated version, biopsy device (14) may be used with any of selected access openings (412) with or without the need to rotate guide cube (402). In use, when the combination of cannula (94) and obturator (92) (or needle (90)) is inserted into a selected access opening (412), the nature of elastomeric body (408) surrounding access opening (412) is such that elastomeric body (408) may compresses to accommodate the volume of the introduced combination of cannula (94) and obturator (92) (or needle (90)). It should be understood that entire length of canula (94) (or needle (90)) need not be inserted into a guide hole or access opening (412) and that in some versions only a portion of the length of cannula (94) (or needle (90)) may be inserted into the guide holes or access openings (412). In some versions nearby access openings (412) or guide holes that do not receive the combination of cannula (94) and obturator (92) (or needle (90)) may compress upon the insertion of the combination of cannula (94) and obturator (92) (or needle (90)) into the selected access opening (412). In some versions, where guide cube (402) is inserted into a grid plate opening, the insertion of the combination of cannula (94) and obturator (92) (or needle (90)) into access opening (412) causes elastomeric body (408) to exert further force against the walls of the grid plate that define the grid plate opening. It will be appreciated based on the teachings herein that elastomeric body (408) and access openings (412) may work together to provide a sufficient outward force from guide cube (402) to the walls defining the grid plate opening such that guide cube (402) fits within the grid plate opening securely both during insertion of the combination of cannula (94) and obturator (92) (or needle (90)) through access opening (412) and during withdrawal of cannula (94) (or needle (90)) through access opening (412).

It should be understood that guide cubes (400, 402) shown in FIGS. 18-19 may be rotatable about one, two, or three axes to provide a desired orientation of passageways defined by slits (410) or openings (412) relative to grid plate (96). For instance, in the versions depicted in FIGS. 18-19, guide cubes (400, 402) may be rotatable about an axis extending through face (414, 420), among other axes. While slits (410) and openings (412) are shown in FIGS. 18-19 as being substantially equidistantly spaced and distributed across face (414, 420), any other suitable arrangements or positioning may be provided. In addition, while slits (410) and openings (412) only provide passageways from one face (414, 420) to an opposing face (not shown), it should be understood that slits (410) or openings (412) may additionally be provided in other faces of guide cubes (400, 402). Still other suitable variations of guide cubes (400, 402) will be apparent to those of ordinary skill in the art in view of the teachings herein.

Figure 20:
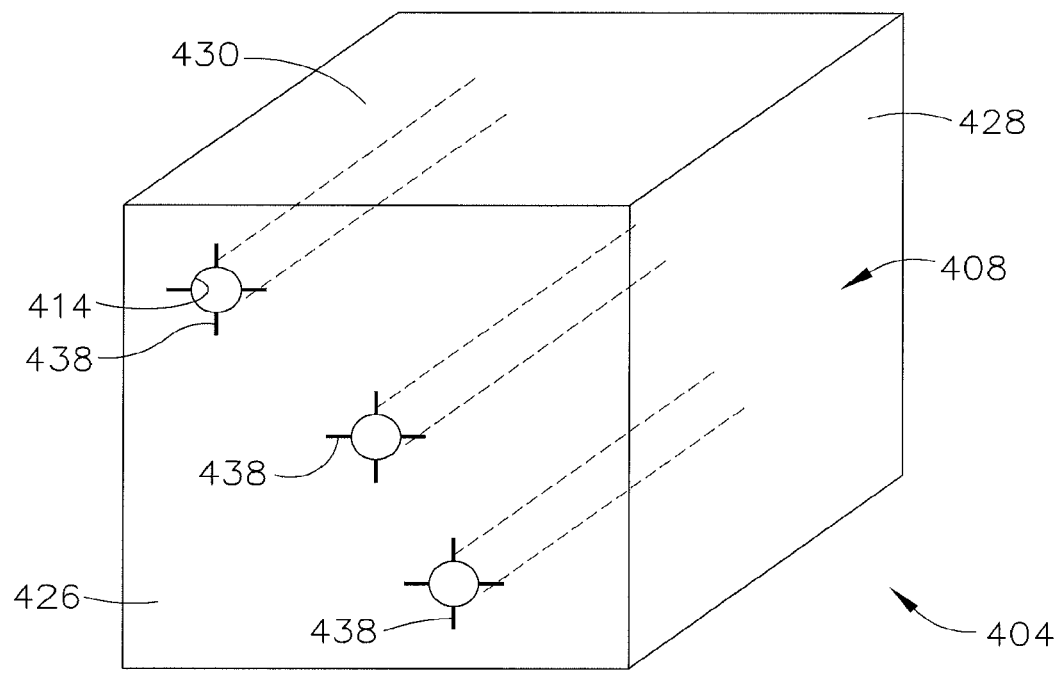
FIG. 20 is a perspective view of another guide cube having an elastomeric body and three reduced sized guide holes that incorporate features that may expand to accommodate a portion of a biopsy device.
Figure 21:
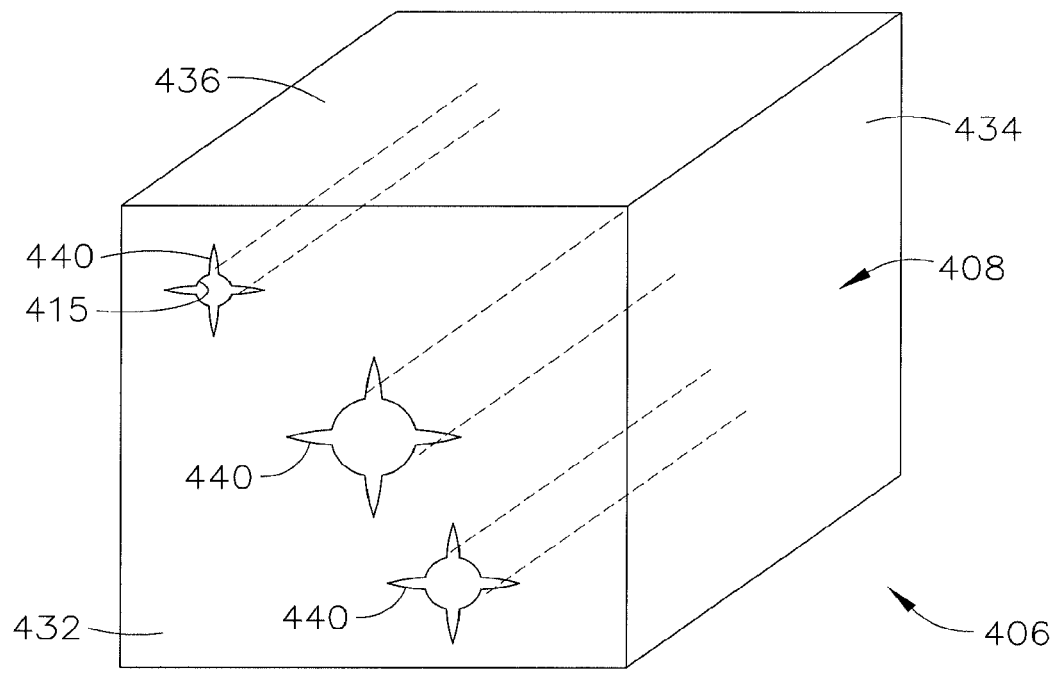
FIG. 21 is a perspective view of another guide cube having an elastomeric body and three reduced sized star-shaped guide holes that may expand to accommodate a portion of a biopsy device.

Referring now to FIGS. 20 and 21, guide cubes (404, 406) may be rotatable (e.g., about one, two, or three axes) and have guide holes (414, 415) that extend between opposing faces of guide cube (404, 406) to provide passageways between opposing faces of guide cube (404, 406). As shown, some versions may include guide cubes (404, 406) having three guide holes (414, 415), still other versions may include either more or fewer guide holes (414, 415). Guide holes (414, 415) may define a relaxed diameter that is less than the diameter of cannula (94) or needle (90), but may further include a feature that allows for expansion of guide holes (414, 415) when the combination of cannula (94) and obturator (92) (or needle (90)) is inserted. In some cases, the presence of an expanding feature may reduce skiving when inserting the combination of cannula (94) and obturator (92) (or needle (90)). As shown in FIG. 20, guide holes (414) include slits (438) that expand when the combination of cannula (94) and obturator (92) (or needle (90)) is inserted. As shown in FIG. 21, guides holes (415) may have a star-shape where extending flares (440) may expand when the combination of cannula (94) and obturator (92) (or needle (90)) is inserted.

As noted above with respect to guide cubes (400, 402), guide cubes (404, 406) may be rotatable about one, two, or three axes to provide a desired orientation of passageways defined by guide holes (414, 415) relative to grid plate (96).

For instance, in the versions depicted in FIGS. 20-21, guide cubes (404, 406) may be rotatable about an axis extending through face (426, 432), among other axes. Furthermore, guide holes (414, 415) may have any suitable arrangement or positioning that is different from the arrangements shown in FIGS. 20-21. In addition, guide holes (414, 415) only provide passageways from one face (426, 432) to an opposing face (not shown), it should be understood that guide holes (414, 415) may additionally be provided in other faces of guide cubes (404, 406). Still other suitable variations of guide cubes (404, 406) will be apparent to those of ordinary skill in the art in view of the teachings herein.

In some versions of guide cubes (400, 402, 404, 406) having an elastomeric body (408), multiple durometers may be used when creating body (408). In some such versions, the multiple durometer design may prevent rotation, angulation, or other movement of the inserted portion of biopsy probe (14) when in use. For example, the inner portion of slits (410) or star-shaped openings (412) may be harder than other portions of body (408) to prevent angulation or movement of biopsy device (14), while the outer grid-contacting portions of body (408) may be softer to allow for greater compatibility of fit with multiple grid plate versions. Similarly, guide holes (414, 415) of guide cubes (404, 406) may be harder than other portions of body (408) to prevent angulation or movement of biopsy device (14), while the outer grid-contacting portions of the body (408) may be softer to allow for greater compatibility of fit with multiple grid plate versions. In some versions guide cubes (400, 402, 404, 406) may even have guide holes (414, 415) constructed from a rigid material, e.g. a polycarbonate, to prevent angulation or movement of biopsy device (14). The rigid material of guide holes (414, 415) may then be surrounded by elastomeric body (408) to allow for greater compatibility of fit with multiple grid plate versions or for other purposes.

Still in some other versions guide cubes (400, 402, 404, 406) may have no predefined guide holes or passageways for receiving probe (91) or other components of biopsy device (14). In such versions guide cubes (400, 402, 404, 406) may be penetrable such that the user may define or create a passageway through guide cubes (400, 402, 404, 406). In some such versions the user may define or create a passageway by inserting a combination of cannula (94) and obturator (92) (or needle (90)) through body (408) of guide cube (400, 402, 404, 406). It will be appreciated based on the teachings herein that the construction of guide cubes (400, 402, 404, 406) in versions where the user defines a passageway may be such that body (408) of guide cube (400, 402, 404, 406) is sufficiently weak to be penetrable by combinations of cannula (94) and obturator (92) (or needle (90)), yet at the same time body (408) of the guide cube (400, 402, 404, 406) is sufficiently strong to prevent biopsy device (14) from unwanted angulation or other undesired movement after insertion. In some user-defined passageway versions of guide cubes, guide cube (400, 402, 404, 406) may be constructed from an elastomeric material, rigid material, or combinations of these or other suitable materials.

Based on the teachings herein, those of ordinary skill in the art will appreciate that several elastomeric materials may be suitable for use with guide cubes (400, 402, 404, 406). By way of example only, suitable elastomeric materials may include thermosetting plastics that may require vulcanization, thermoplastic elastomers (e.g. Santoprene™ among others), natural rubber, synthetic rubbers (e.g. ethylene propylene diene M-class—EPDM—among others), and other polymers having suitable elastic properties.

In some versions, the elastomeric used for body (408) may be imbedded or coated with a lubricant. The lubricant may make it easier to insert and remove the combination of cannula (94) and obturator (92) (or needle (90))) from guide cubes (400, 402, 404, 406) and further reduce the potential for skiving.

Creating guide cubes (400, 402, 404, 406) having elastomeric body (408) may be accomplished in a variety of ways. For example, in some versions a multi-shot molding process may be used where an inner portion of body (408) of guide cubes (400, 402, 404, 406) may be molded from a first material having a first durometer, and an outer portion of body (408) may be molded from a second material having a second durometer. In some other versions, elastomeric body (408) may be manufactured as separate parts later coupled together to form body (408). In such a version, the parts of body (408) may be coupled together by mechanical fastening, chemical adhesive, or other suitable bonding or coupling techniques. Still it should be appreciated that body (408) may be molded or extruded as a single unitary piece having a uniform composition of elastomeric material.

Based on the teachings herein, those of ordinary skill in the art will appreciate that the configuration of elastomeric body (408), the types of elastomeric materials used for body (408), the application processes used to create elastomeric body (408), and other factors may influence whether or not a specific elastomeric body design is suitable. Those of ordinary skill in the art, based on the teachings herein, will further appreciate that suitable designs for guide cubes having an elastomeric body may create a secure interference between a grid plate and the guide cube without significantly increasing the force required to insert or remove the guide cube from the grid plate. Accordingly, guide cubes (400, 402, 404, 406) of the present example may fit in various types of grid plates having grid openings or recesses of various sizes or configurations. It should also be understood that, in some settings, the elastomeric properties of body (408) may provide sufficient friction with a grid plate to reduce the likelihood that guide cube (400, 402, 404, 406) will undesirably fall out of the grid plate. Furthermore, it will be appreciated based on the teachings herein that suitable designs for a guide cube having an elastomeric body may create a secure interface between a probe or other components of a biopsy device and a corresponding guide hole or access port of the body.

In some versions of guide cubes (400, 402, 404, 406) having elastomeric body (408), additional self-grounding features as discussed above may be included. For instance rectangular prism self-grounding member (240, 260, 330) may be adapted for use with guide cubes (400, 402, 404, 406). In other versions, guide cubes (400, 402, 404, 406) may incorporate enlarged hat portion (270) as a self-grounding feature. It should be appreciated that the self-grounding features may or may not be comprised of elastomeric material. Furthermore, it should be appreciated that the self-grounding features may be entirely omitted from guide cubes (400, 402, 404, 406) in lieu of other grounding features incorporated with a grid plate or other components. Still, it should be appreciated that elastomeric body (408) itself may serve as the self-grounding feature for guide cubes (400, 402, 404, 406). In such a version, the outward force exerted by elastomeric body (408) against the inner walls of the grid plate may provide the grounding feature holding guide cubes (400, 402, 404, 406) securely in place. Still other suitable features, configurations, components, functionalities, operability, and variations of guide cube (400, 402, 404, 406) will be apparent to those of ordinary skill in the art in view of the teachings herein.

E. Elastomeric Body with Malleable Members

Figure 22:
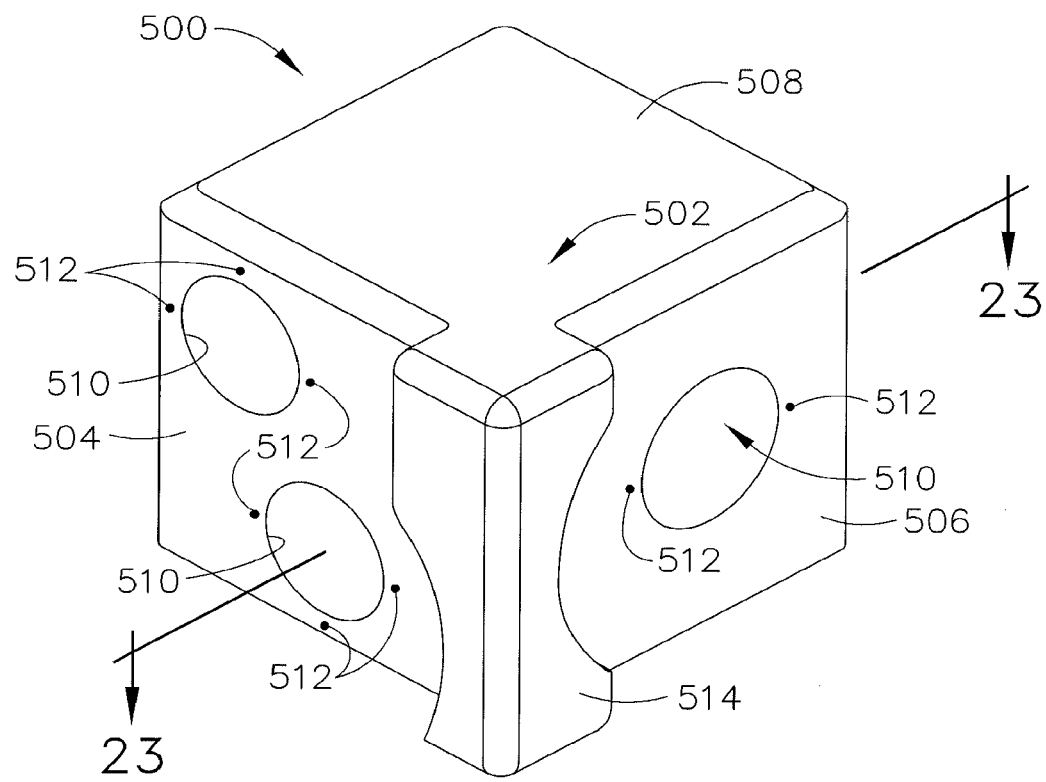
FIG. 22 is a perspective view of another guide cube having an elastomeric body and malleable members adjacent and parallel to guide holes of the guide cube.
Figure 23:
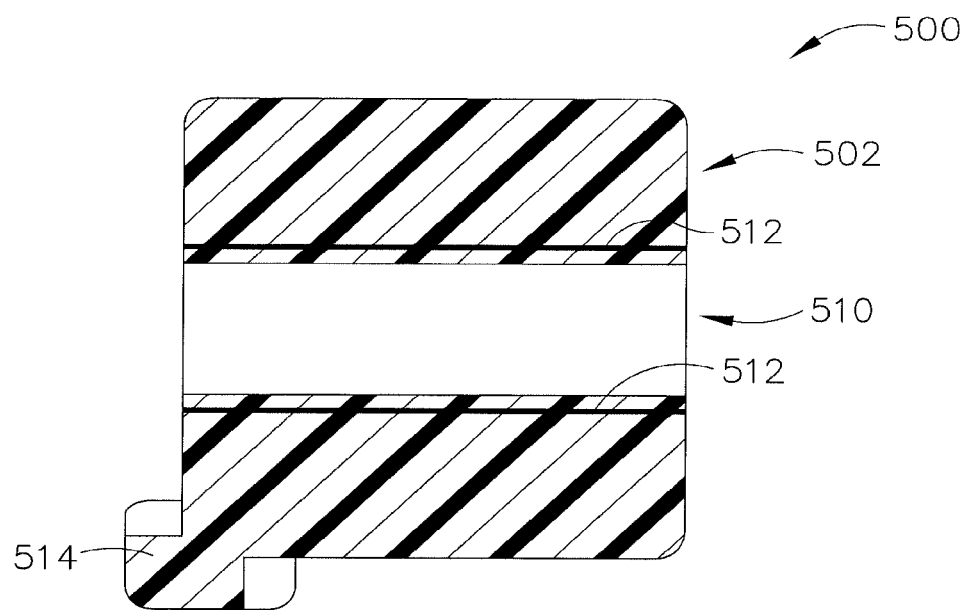
FIG. 23 is a top cross-section view of the guide cube of FIG. 22 taken along line 23-23 shown in FIG. 22.

FIGS. 22 and 23 depict another exemplary version of a guide cube (500). Some versions of guide cube (500) may facilitate the ability to angle probe (91) and/or other components of biopsy device (14) and maintain the desired angle. In the illustrated version, guide cube (500) comprises body (502) defined by pairs of opposing faces that include faces (504, 506, 508) and other faces (not shown). Body (502) may be constructed wholly or partially from an elastomeric material, as discussed above or otherwise.

Guide cube (500) may further include one or more guide holes (510) that provide passageways between pairs of opposing faces, e.g. face (504) and its opposing face (not shown), and face (506) and its opposing face (not shown). Referring to FIG. 22, guide holes (510) may initially be positioned perpendicular to the associated pair of opposing faces. Adjacent and parallel to each guide hole (510) are wires (512) in the present example. Wires (512) may be overmolded or substantially surrounded by the elastomeric material comprising body (502) of guide cube (500). Alternatively, wires (512) may be inserted into body (502) or otherwise provided in body (502). Wires (512) may be made from a non-magnetic material such that no MRI artifact, or only a minimal MRI artifact, will occur during an associated imaging procedure. Some suitable materials for wires (512) may include, but are not limited to, cobalt alloys such as cobalt L605, aluminum alloys such as aluminum 6061, stainless steel alloys such as 316L stainless steel, titanium alloys such as titanium 6, nickel-cobalt alloys such as MP35N, and other suitable alloys. Alternatively, wires (512) may be formed of any other suitable materials or combinations of materials.

In use, the combination of cannula (94) and obturator (92) (or needle (90))) may be inserted through one of guide holes (510). To the extent that a combination of cannula (94) and obturator (92) is used, obturator (92) may then be removed from cannula (92), and needle (90) may then be inserted in cannula (94). Biopsy device (14) may then be angled to a desired position (e.g., providing a desired angular orientation of needle (90)). The action of angling biopsy device (14) may cause wires (512) to undergo a plastic deformation such that wires (512) are malleable and hold their position once biopsy device (14) reaches a desired orientation. The elastomeric nature of body (502) of guide cube (500) allows body (502) to conform to the angled orientation of biopsy device (14). Moreover, the construction of guide cube (500) may be such that wires (512), once in their bent position, withstand any biasing forces by body (502) that may attempt to return guide cube (500) to its initial state. In such versions, the angled orientation of inserted biopsy device (14) may thus be maintained without the user or another person or apparatus holding biopsy device (14) at the desired position. Of course, in settings where an obturator (92) and cannula (94) are used, a user may first obtain a desired angular orientation with either cannula (94) or the combination of obturator (92) and cannula (94) before inserting needle (90) into cannula (94). It should also be understood that a user need not necessarily adjust the angle of cannula (94) or needle (90) in guide cube (500), as wires (512) may simply reinforce a substantially horizontal orientation or other predefined orientation.

Guide cube (500) may further include a self-grounding member, such as rectangular prism (514) shown in FIGS. 22 and 23. However, it should be appreciated based on the teachings herein that other suitable grounding features may be used in addition to or instead of rectangular prism (514). Furthermore, it should be appreciated that guide cube (500) may be rotatable to provide various guide hole (510) orientations even though guide cube (500) is configured to permit angling an inserted biopsy device (14).

Based on the teachings herein, those of ordinary skill in the art will appreciate that several elastomeric materials may be suitable for use with guide cube (500). By way of example only, suitable elastomeric materials may include thermosetting plastics that may require vulcanization, thermoplastic elastomers (e.g. Santoprene™ among others), natural rubber, synthetic rubbers (e.g. ethylene propylene diene M-class—EPDM—among others), and other polymers having suitable elastic properties.

Creating guide cube (500) with body (502) may be accomplished in a variety of ways. For example, in some versions molding process may be used where a first molding process creates guide holes (510). Then wires (512) may be placed around the guide holes (510), followed by a second molding process that over-molds wires (512) and guide holes (510) with material that comprises body (502). In other versions, guide cube (500) may be molded or extruded as a single solid structure. Then bores may be made in guide cube (500) by any suitable technique to create guide holes (510). Then wires (512) may pierce body (502) to be inserted into body (502) alongside guide holes (510). Those of ordinary skill in the art will appreciate, based on the teachings herein, various other ways to create guide cube (500) of FIGS. 22 and 23, including but not limited to various other ways to position wires (512) in body (502).

As noted above with respect to guide cubes (400, 402, 404, 406), guide cube (500) may be rotatable about one, two, or three axes to provide a desired orientation of passageways defined by guide holes (510) relative to grid plate (96). For instance, in the versions depicted in FIGS. 22-23, guide cube (500) may be rotatable about axes extending through faces (504, 506), among other axes. Furthermore, guide holes (510) may have any suitable arrangement or positioning that is different from the arrangements shown in FIGS. 20-21. In addition, guide holes (510) only provide passageways from one face (504, 506) to an opposing face (not shown), it should be understood that guide holes (510) may additionally be provided in other faces of guide cube (500). Still other suitable variations of guide cube (500) will be apparent to those of ordinary skill in the art in view of the teachings herein.

Those of ordinary skill in the art, based on the teachings herein, will further appreciate that suitable versions of guide cube (500) having elastomeric body (502) may improve fit and compatibility of guide cube (500) with various grid plates by creating a secure interference between the grid plate and guide cube (500) without significantly increasing the force required to insert or remove guide cube (500) from the grid plate. Accordingly, guide cube (500) of the present example may fit in various types of grid plates having grid openings or recesses of various sizes or configurations. It should also be understood that, in some settings, the elastomeric properties of body (502) may provide sufficient friction with a grid plate to reduce the likelihood that guide cube (500) will undesirably fall out of the grid plate. Furthermore, it will be appreciated based on the teachings herein that suitable versions for guide cube (500) may create a secure interface between cannula (94), probe (91), or other components of biopsy device (14) and the corresponding guide hole (510) of body (502), such that biopsy device (14) does not slip within guide hole (510) during use. In addition, other suitable features, configurations, components, functionalities, operability, and variations of guide cube (500) will be apparent to those of ordinary skill in the art in view of the teachings herein. It should also be understood that any other guide cube described herein, and variations thereof, may include one or more wires (512) if desired, including but not limited to guide cubes (400, 402, 404, 406).

F. Tapered Guide Cubes

Figure 24:
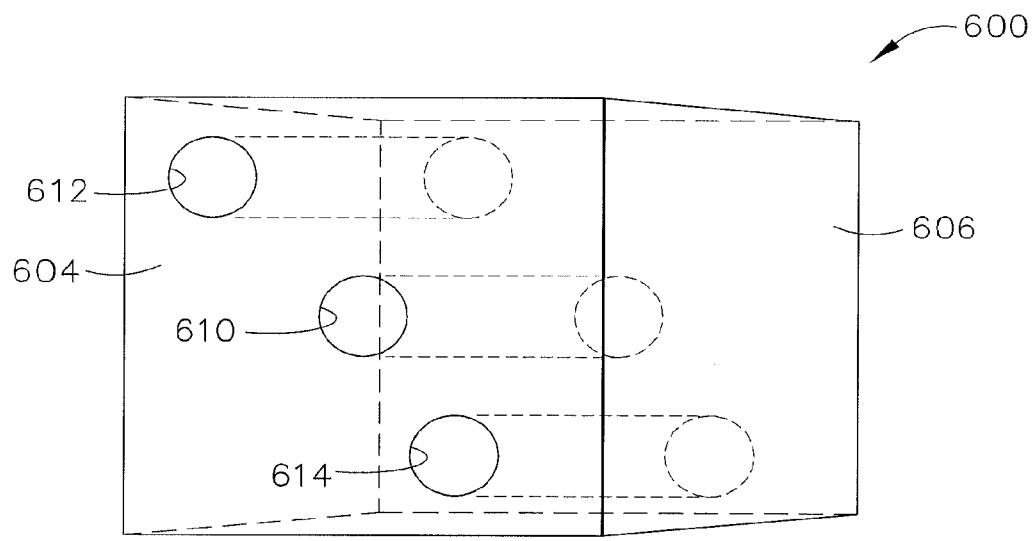
FIG. 24 is a perspective view of another guide cube having a pair of tapered sides.
Figure 25:
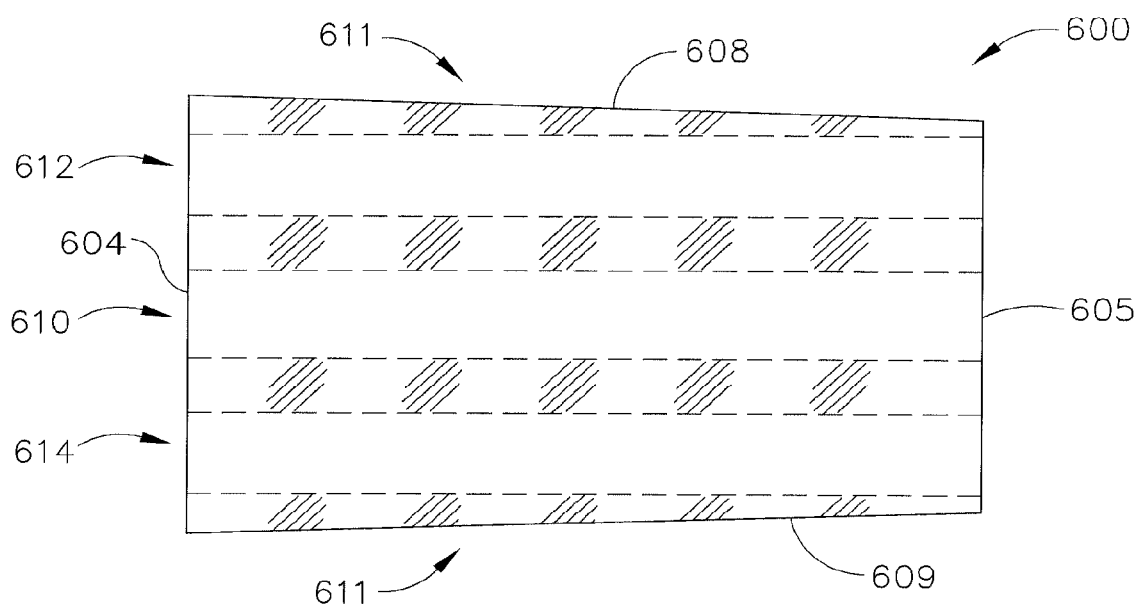
FIG. 25 is a side cross-sectional view of the guide cube of FIG. 24, showing the guide holes in phantom.

FIGS. 24-27 show other versions of guide cubes (600, 602) incorporating a tapered feature to create guide cubes (600, 602) that conform to grid plates of various designs. Referring to FIGS. 24 and 25, guide cube (600) includes pairs of opposing faces that include faces (604, 605, 606, 608, 609) and other faces (not shown). Guide cube (600) further includes central guide hole (610), corner guide hole (612), and off-center guide hole (614), which pass orthogonally between face (604) and face (605) to provide respective passageways through faces (604, 605). As shown in the cross-section view in FIG. 25, face (604) and face (605) have unequal dimensions that create a taper from one side of guide cube (600) to the other side of guide cube (600). In use with a grid plate, the tapered sides (611) of guide cube (600) may permit guide cube (600) to securely interface with the opening in the grid plate by inserting guide cube (600) in the grid plate up to the point where the tapered sides (611) contact the interior walls of the opening in the grid plate. In some settings, such an interface may be securely provided regardless of whether the interior walls of the opening in the grid plate are substantially horizontal and vertical along their length or at non-horizontal and/or non-vertical angles along their length.

Based on the teachings herein, those of ordinary skill in the art will appreciate that additional grounding features may be incorporated or used with guide cube (600). For example, in some versions, guide cube (600) may be substantially rigid throughout. In some other versions, (e.g., where guide cube (600) is formed of a substantially rigid material), guide cube (600) may be fitted with elastomeric edges around the tapered sides (611), thereby providing some degree of compression force to further secure guide cube (600) in the grid plate. Guide holes (610, 612, 614) may also have an elastomeric material therein, in addition to or in lieu of having elastomeric material at the edges and/or faces (604, 605, 606, 608, 609) of guide cube (600). In still other versions, guide cube (600) may have an elastomeric body capable of compression fitting within a grid plate. In some versions of tapered guide cube (600) incorporating an elastomeric body, a multi-step molding process may be used to achieve guide holes (610, 612, 614) having a higher durometer or more rigidity than the elastomeric body portion itself.

It should further be appreciated that guide cube (600) may comprises more than one pair of tapered sides (611). For example, opposing side pair comprised of face (606) and opposing face (not shown) may also be tapered, in addition to or in lieu of one or both sides (611) being tapered. Alternatively, guide cube (600) may have just one tapered side (611). Still yet in other versions guide cube (600) may include more than three pairs of opposing faces, thereby having a shape other than a six-sided cube. In such versions, one, some, or all of the sides may or may not be tapered. Still other suitable features, configurations, components, functionalities, operability, and variations of guide cube (600) will be apparent to those of ordinary skill in the art in view of the teachings herein.

Figure 26:
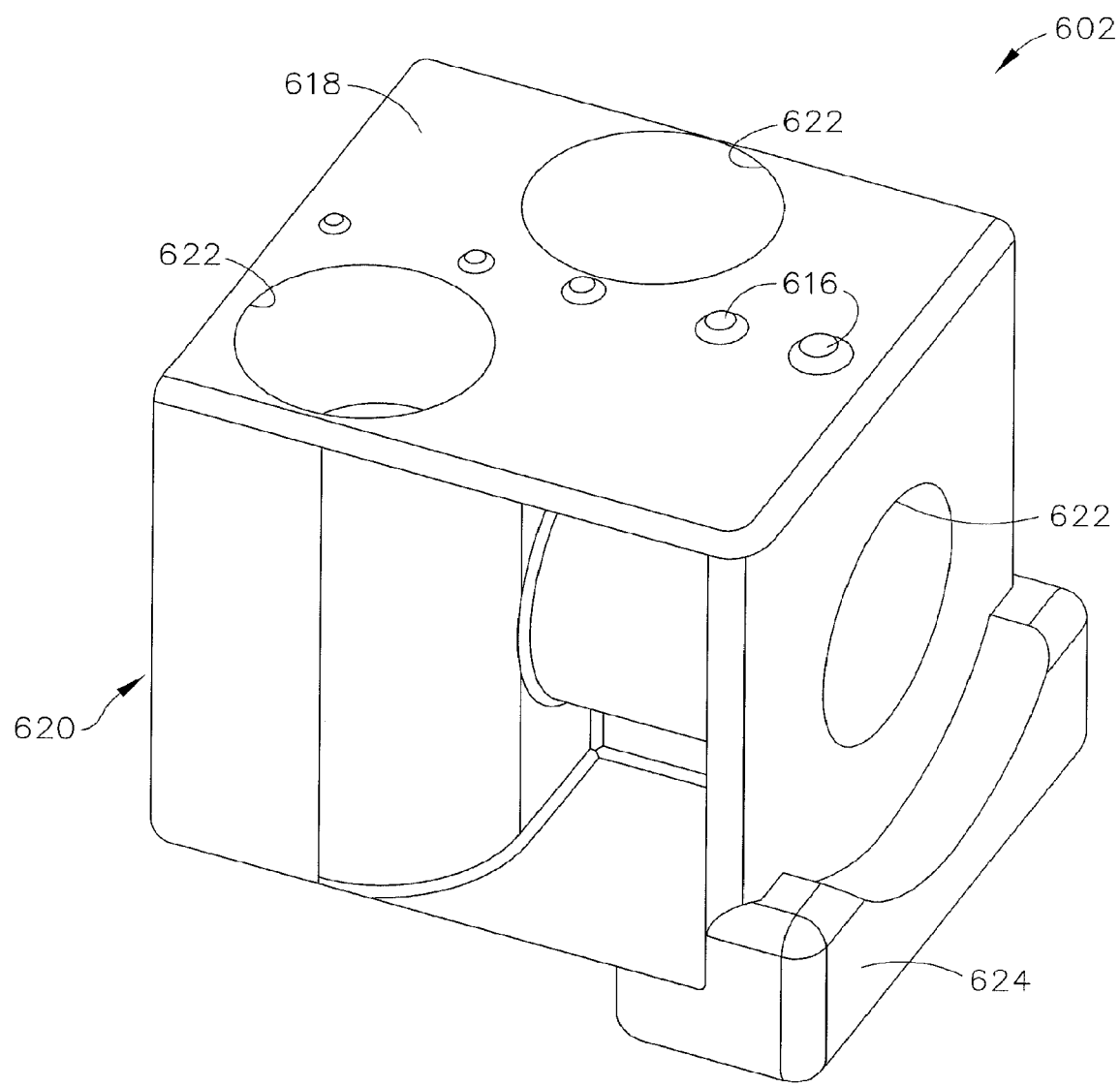
FIG. 26 is a perspective view of another guide cube having a set of elastomeric bumps that provide a taper profile to the guide cube.
Figure 27:
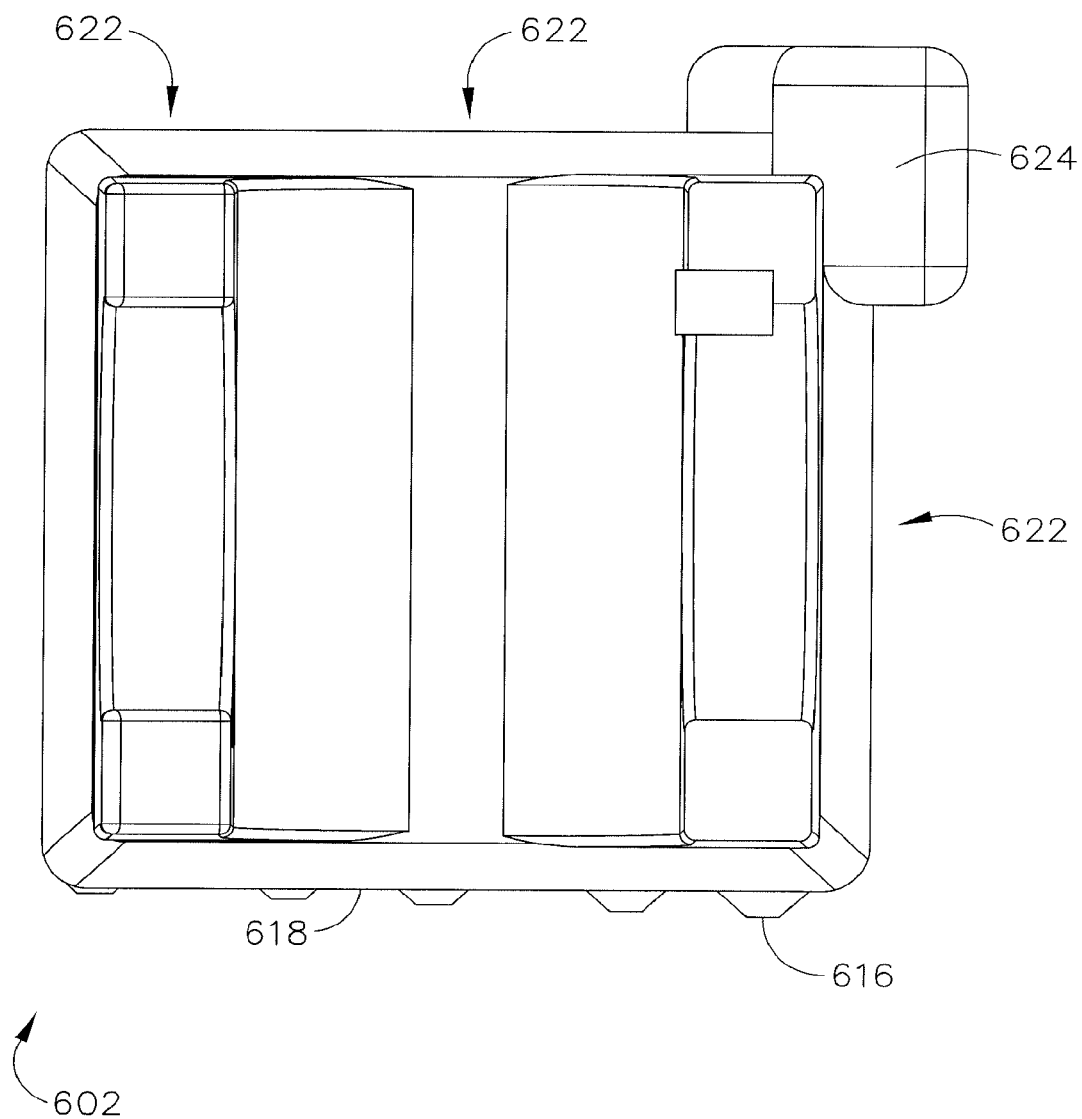
FIG. 27 is a side view of the guide cube of FIG. 26.

Referring now to FIGS. 26 and 27, guide cube (602) includes set of elastomeric bumps (616) that increase in height proximally as guide cube (602) is inserted in a grid plate. Elastomeric bumps (616) create a taper along face (618) of guide cube (602). The taper allows guide cube (602) to fit in multiple grid plates (e.g., different types of grid plates having differently sized openings). While FIGS. 26 and 27 show elastomeric bumps (616) on one face (618) of guide cube (602), in other versions elastomeric bumps (616) may be located on any or all faces of guide cube (602).

Guide cube (602) further comprises body (620) that may be constructed from a rigid material. However, based on the teachings herein, it will be appreciated that body (620) may be constructed from an elastomeric material, partially constructed from an elastomeric material, or constructed from any other suitable type of material (including combinations of materials having similar or different properties). Regardless of the construction of body (620), it will be appreciated based on the teachings herein that the guide holes (622) of the present example may be constructed from a material that prohibits or at least restricts unwanted angulation or movement of inserted probe (91) and/or other components of biopsy device (14). For instance, such restriction or prohibition may be provided by the rigidity of body (620). Alternatively, such as in versions where body (620) is formed of an elastomeric material, such restriction or prohibition may be provided by a rigid sleeve inserted through guide holes (622), by one or more wires (512) positioned near guide holes (622), or in any other suitable fashion.

As shown in FIGS. 26 and 27, guide cube (602) may further include rectangular prism (624) self-grounding feature. The self-grounding feature may be located along a corner of guide cube (602) and at a proximal end of guide cube (602) where elastomeric bumps (616) have the greatest height. This arrangement may help ensure that elastomeric bumps (616) interface with the grid plate and compress accordingly until rectangular prism (624) contacts the grid plate and blocks guide cube (602) from further insertion. It should also be understood that elastomeric bumps (616) may provide some degree of compression force to further secure guide cube (600) in the grid plate. Furthermore, the elastomeric properties of bumps (616) may provide sufficient friction with a grid plate to reduce the likelihood that guide cube (602) will undesirably fall out of the grid plate. It should also be understood that any other guide cube described herein, and variations thereof, may include one or more bumps (616) or similar features, if desired. Still other suitable features, configurations, components, functionalities, operability, and variations of guide cube (602) will be apparent to those of ordinary skill in the art in view of the teachings herein.

G. Hinged Guide Cubes

Figure 28:
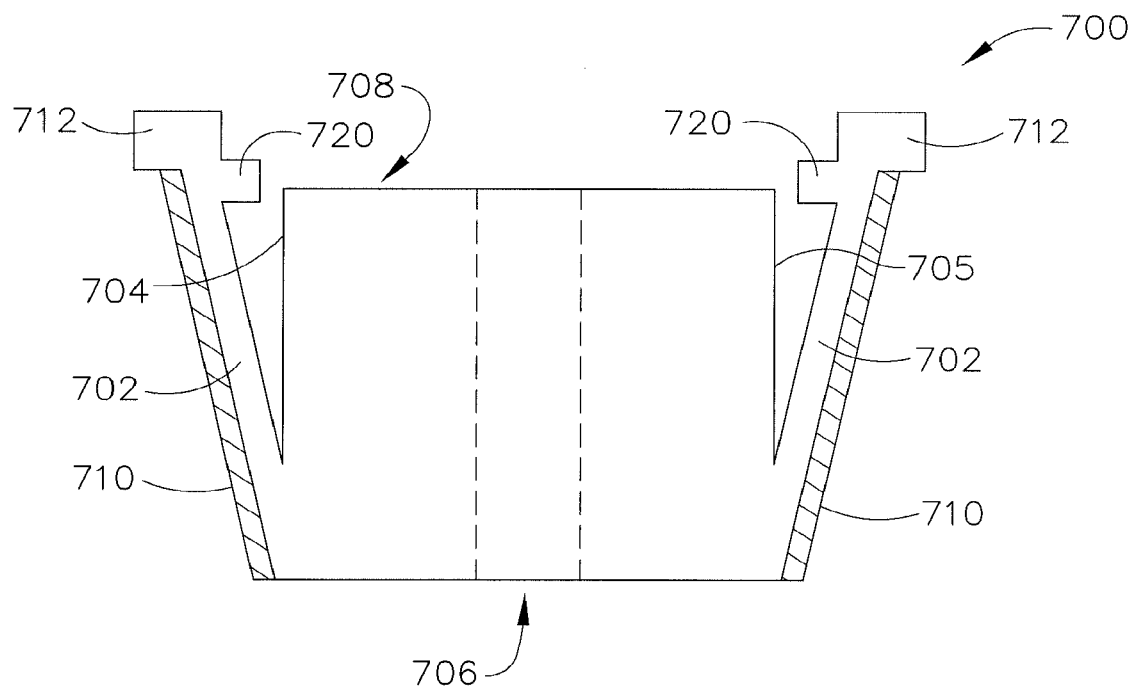
FIG. 28 is a side view of another guide cube having hinge members extending along a pair of sides and showing a central guide hole in phantom.
Figure 29:
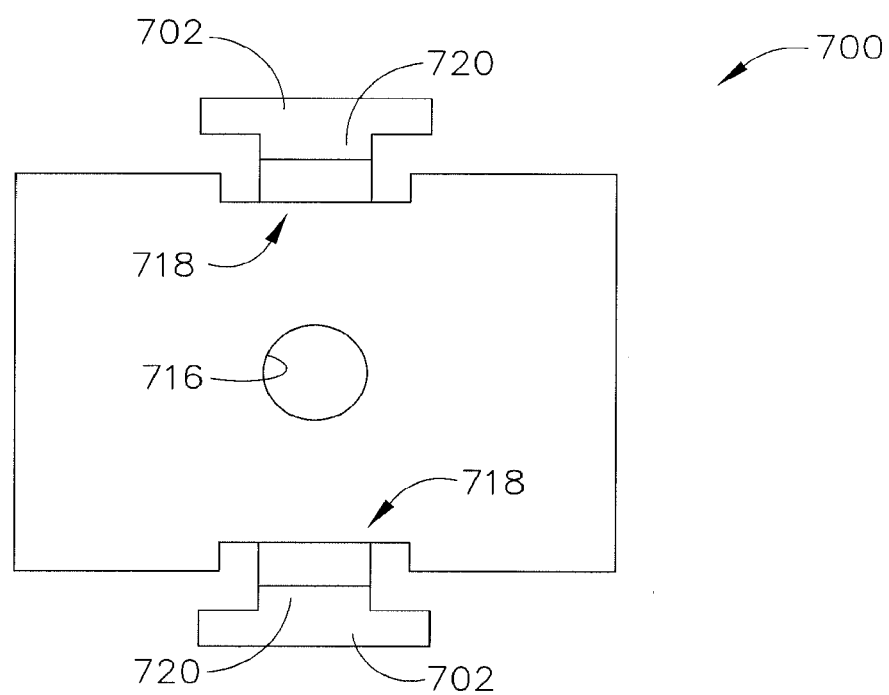
FIG. 29 is a front view of the guide cube of FIG. 28.
Figure 30:
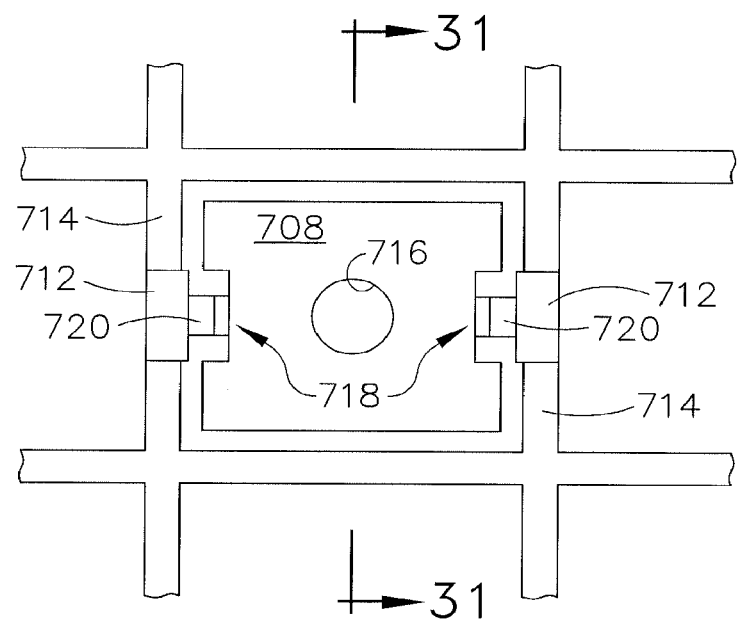
FIG. 30 is a front view of the guide cube of FIG. 28 inserted into a grid plate, with the grid plate shown partially.
Figure 31:
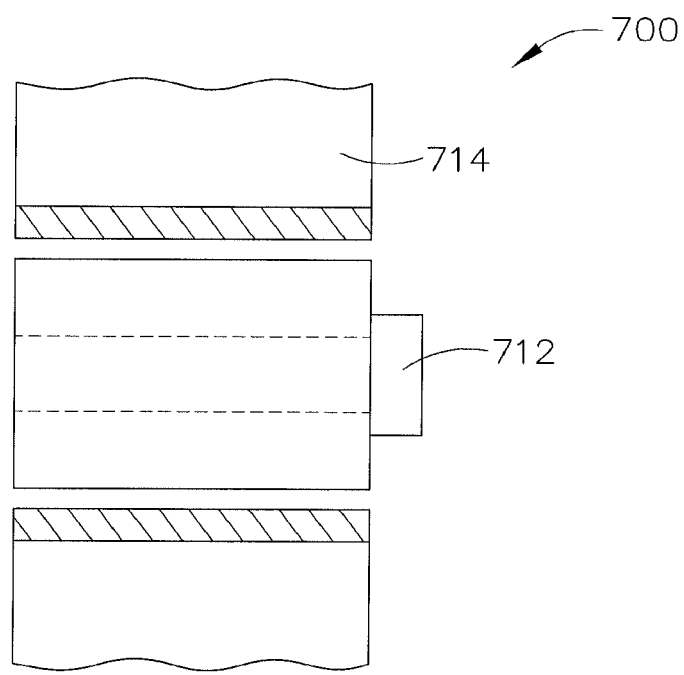
FIG. 31 is side view of the guide cube and grid plate of FIG. 30, showing the grid plate in a cross-section taken along line 31-31 of FIG. 30 and showing the central guide hole of the guide cube in phantom.

FIGS. 28-31 depict guide cube (700) having hinge members (702) that permit guide cube (700) to fit within grid plates having different opening dimensions. As shown in FIG. 28, guide cube (700) includes hinge members (702) along a pair of opposing faces comprising face (704) and face (705). Hinge members (702) originate from distal end (706) of guide cube (700) and extend at an angle proximally past proximal face (708) of guide cube (700) defining a taper relative to face (704) and face (705) of guide cube (700). Each hinge member (702) may include outer elastomeric surface (710) that engages the interior walls of a grid plate when guide cube (700) is inserted into an opening in a grid plate. Each hinge member (702) may also include shoulder portion (712) that extends past proximal face (708) as shown in FIGS. 28 and 31. Hinge members (702) of the present example are coupled with the remainder of guide cube (700) by living hinges that are resiliently biased to extend hinge members (702) outwardly as shown in FIG. 28. In addition or in the alternative, hinge members (702) themselves may be resiliently biased to extend outwardly. When guide cube (700) is inserted into a grid plate, shoulder portions (712) overlap grid lines (714) defining the opening of the grid plate and thus prevent over-insertion of guide cube (700) as shown in FIG. 30. Elastomeric surfaces (710), together with the resilient outward bias of hinge members (702), may provide sufficient friction with a grid plate to reduce the likelihood that guide cube (700) will undesirably fall out of the grid plate.

In one example of operation, a user pinches hinge members (702) toward a center of guide cube (700) that may be indicated by central guide hole (716). Then the user inserts guide cube (700) into a selected opening in the grid plate, pushing guide cube (700) distally toward the patient and at the same time releasing hinge members (702). As guide cube (700) is being inserted, hinge members (702) resiliently push away from the center of guide cube (700) and contact the interior walls defining the opening in the grid plate. Elastomeric surfaces (710) of hinge members (702) may compress against the interior walls that define the opening in the grid plate thereby securely fitting guide cube (700) within the grid plate. To release guide cube (700) from the grid plate, a user grasps shoulder portions (712) of hinge members (702), depressing hinge members (702) toward the center of guide cube (700). As shown in FIGS. 29 and 30, proximal face (708) of guide cube (700) may include cut-out portions (718) that make room for proximal end protrusions (720) of hinge members (702) when hinge members (702) are pinched. With hinge members (702) pinched, elastomeric surfaces (710) may disengage the grid plate and guide cube (700) may be pulled out from the grid plate.

Guide cube (700) may include any suitable arrangement of guide holes and need not be limited to only including central guide hole (716) as in the illustrated version. In some versions, guide cube (700) may include nine individual guide holes arranged in three rows of three guide holes each. In some other versions, guide cube (700) may include one or more guide holes and guide cube (700) may be rotatable to provide for alternate guide hole orientations. In still other versions, guide cube (700) comprises slits or similar features instead of guide holes, to provide a passageway between opposing faces. It should be appreciated that some versions may include hinge members (702) that may be detachable from guide cube (700) to permit rotation of guide cube (700) such that a face other than face (708) is positioned proximally within the grid plate. In such versions, hinge members (702) may be re-attached along other faces of guide cube (700) besides just faces (704, 705). It is also noted that guide cube (700) may be formed of a substantially rigid material, of an elastomeric material, and/or of any other suitable material, including combinations of materials. Still other suitable features, configurations, components, functionalities, operability, and variations of guide cube (700) will be apparent to those of ordinary skill in the art in view of the teachings herein. It should also be understood that any other guide cube described herein, and variations thereof, may include one or more hinge members (702) if desired.

While several guide cubes have been discussed in detail above, it should be understood that the components, features, configurations, and methods of using the guide cubes discussed are not limited to the contexts provided above. In particular, components, features, configurations, and methods of use described in the context of one of the guide cubes may be incorporated into any of the other guide cubes. One merely exemplary additional feature that may be provided in any of the guide cubes described herein is one or more ridges on one or more external faces of the cube. Such ridges may be substantially rigid, elastomeric, or have any other suitable properties. Such ridges may provide a more secure fit between a cube and grid (e.g., reducing the likelihood that the guide cube will undesirably fall out of the grid plate), may permit a single cube to be inserted in different grids having differently sized openings, and/or may provide other results. Still other additional and alternative suitable components, features, configurations, and methods of using the guide cubes will be apparent to those of ordinary skill in the art in view of the teachings herein.

Versions of the present invention have application in conventional endoscopic and open surgical instrumentation as well as application in robotic-assisted surgery.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A guide device insertable into an aperture of a grid plate for guiding a medical instrument relative to a patient, the guide device comprising:
   (a) a body defined by a plurality of faces, wherein the body comprises a proximal portion and a distal portion, wherein the body is comprised of a first material having a first durometer, and wherein the body is further comprised of a second material having a second durometer, wherein the first durometer is different from the second durometer;

(b) at least one passageway, wherein the at least one passageway is comprised of the first material, wherein the at least one passageway extends from the proximal portion through the body and to the distal portion, wherein the at least one passageway is configured to receive at least a portion of the medical instrument; and (c) a pair of hinged members coupled to the body, wherein the pair of hinged members are operably configured to interface with a surface of the grid plate to provide a secure fit of the guide device within the aperture of the grid plate.

2. The guide device of claim 1, wherein the pair of hinged members are positionable in a first state and a second state, wherein in the first state the pair of hinged members do not exert force on an interior wall of the grid plate defining the aperture of the grid plate, and wherein in the second state the pair of hinged members do exert force on the interior wall of the grid plate defining the aperture.

3. The guide device of claim 2, wherein the pair of hinged members each comprise an outer surface, wherein the outer surfaces are configured to contact the interior wall of the grid plate defining the aperture, wherein the outer surfaces comprise a compressible portion.

4. The guide device of claim 3, wherein the at least one passageway is comprised of a rigid material, and wherein the body surrounding the rigid material is comprised of a compressible material.

5. The guide device of claim 1, wherein each of the hinged members comprise a living hinge, wherein the living hinges pivotably couple the hinged members to the body.

6. The guide device of claim 1, further comprising a grounding structure operatively configured to prevent over-insertion of the guide device into the grid plate.

7. The guide device of claim 1, wherein the pair of hinged members each comprise a protruding portion, wherein the protruding portions are operably configured to contact the grid plate to prevent over-insertion of the guide device.

8. The guide device of claim 1, wherein the pair of hinged members are selectively detachable from the body of the guide device, wherein the pair of hinged members are further configured to selectively attach to a plurality of faces of the body.

* * * * *